United States Patent
Williams et al.

(10) Patent No.: US 9,617,239 B2
(45) Date of Patent: *Apr. 11, 2017

(54) PHENOXY THIOPHENE SULFONAMIDES AND THEIR USE AS INHIBITORS OF GLUCURONIDASE

(75) Inventors: Alfred L. Williams, Durham, NC (US); John Scott, Durham, NC (US); Li-An Yeh, Cary, NC (US); Matthew Robert Redinbo, Chapel Hill, NC (US)

(73) Assignees: North Carolina Central University, Durham, NC (US); The University of North Carolina at Chapel Hill, Chapel Hill, NC (US)

( * ) Notice: Subject to any disclaimer, the term of this patent is extended or adjusted under 35 U.S.C. 154(b) by 928 days.

This patent is subject to a terminal disclaimer.

(21) Appl. No.: 13/641,713

(22) PCT Filed: Mar. 10, 2011

(86) PCT No.: PCT/US2011/027974
§ 371 (c)(1),
(2), (4) Date: Sep. 10, 2013

(87) PCT Pub. No.: WO2011/112858
PCT Pub. Date: Sep. 15, 2011

(65) Prior Publication Data
US 2013/0345235 A1    Dec. 26, 2013

Related U.S. Application Data

(60) Provisional application No. 61/312,512, filed on Mar. 10, 2010.

(51) Int. Cl.
| | | |
|---|---|---|
| A61K 31/38 | (2006.01) |
| C07D 333/34 | (2006.01) |
| C07D 409/12 | (2006.01) |
| C07D 413/12 | (2006.01) |
| C07D 417/12 | (2006.01) |
| A61K 31/137 | (2006.01) |
| A61K 31/42 | (2006.01) |
| A61K 31/4409 | (2006.01) |
| A61K 31/4709 | (2006.01) |
| A61K 31/553 | (2006.01) |
| C07D 295/135 | (2006.01) |
| C07D 409/06 | (2006.01) |
| C12Q 1/34 | (2006.01) |

(52) U.S. Cl.
CPC .......... *C07D 333/34* (2013.01); *A61K 31/137* (2013.01); *A61K 31/42* (2013.01); *A61K 31/4409* (2013.01); *A61K 31/4709* (2013.01); *A61K 31/553* (2013.01); *C07D 295/135* (2013.01); *C07D 409/06* (2013.01); *C07D 409/12* (2013.01); *C07D 413/12* (2013.01); *C07D 417/12* (2013.01); *C12Q 1/34* (2013.01); *G01N 2333/924* (2013.01); *G01N 2500/02* (2013.01)

(58) Field of Classification Search
None
See application file for complete search history.

(56) References Cited

U.S. PATENT DOCUMENTS

| | | |
|---|---|---|
| 5,817,800 A | 10/1998 | Bosslet et al. |
| 2001/0021714 A1 | 9/2001 | Chan et al. |
| 2004/0198778 A1 | 10/2004 | Kreft et al. |

OTHER PUBLICATIONS

Williams et al. The Synthesis of Phenoxy Thiophene Sulfonamides. The 60th Southeastern 1—Regional Meeting (SERMACS) Nov. 2008, p. 1—http://acs.confex.com/acs/serm08/techprogram/P64032.HTM.

*Primary Examiner* — Golam M Shameem
*Assistant Examiner* — Laura Daniel
(74) *Attorney, Agent, or Firm* — Ladas & Parry LLP

(57) ABSTRACT

This invention relates generally to compounds that are glucuronidase inhibitors. Glucuronidase inhibitors described include phenoxy thiophene sulfonamides. Other compounds, for instance pyridine sulfonyls, benzene sulfonyls, thiophene sulfonyls, thiazole sulfonyls, thiophene carbonyls, and thiazole carbonyls, are also contemplated. Also contemplated are compositions including one or more of such compounds for use inhibiting glucuronidase and methods of using one or more of such compounds as a co-drug to be used in combination with the anticancer drug CPT-11.

9 Claims, No Drawings

US 9,617,239 B2

PHENOXY THIOPHENE SULFONAMIDES AND THEIR USE AS INHIBITORS OF GLUCURONIDASE

RELATED APPLICATION INFORMATION

This application is a 371 of International Application PCT/US2011/027974 filed 10 Mar. 2011 entitled "Phenoxy Thiophene Sulfonamides And Their Use As Inhibitors Of Glucuronidase" which was published in the English language on 15 Sep. 2011, with International Publication Number WO 2011/112858 A1, and which claims priority from U.S. Provisional Patent Application No. 61/312,512 filed 10 Mar. 2010, the contents of which are incorporated herein by reference.

This invention was supported in part by funds from the U.S. Government (National Cancer Institute 04-051311). The U.S. Government may have certain rights in the invention.

This invention relates generally to compounds that are glucuronidase inhibitors. This invention relates to phenoxy thiophene sulfonamides that inhibit bacterial glucuronidase. Compositions including one or more of such compounds and methods of using one or more of such compounds as a co-drug to be used in combination with a camptothecin-derived anticancer drug.

BACKGROUND

Camptothecin, a plant alkaloid derived from the Chinese *Camptotheca acuminata* tree, was added to the National Cancer Institute's natural products screening set in 1966. It showed strong anti-neoplastic activity but poor bioavailability and toxic side effects. After thirty years of modifying the camptothecin scaffold, two derivatives emerged and are now approved for clinical use[1]. Topotecan (Hycamtin®; GlaxoSmithKline) is currently employed to treat solid ovarian, lung and brain tumors[1]. CPT-11 (also called Irinotecan, and Camptosar®; Pfizer) contains a carbamate-linked dipiperidino moiety that significantly increases bioavailability in mammals[1]. This dipiperidino group is removed from the CPT-11 prodrug in vivo by carboxylesterase enzymes that hydrolyze the carbamate linkage to produce the drug's active metabolite, SN-38[2]. CPT-11 is currently used to treat solid colon, lung and brain tumors, along with refractory forms of leukemia and lymphoma[3].

The sole target of the camptothecins is human topoisomerase I[4]. This enzyme relieves superhelical tension throughout the genome and is essential for DNA metabolism, including DNA replication, transcription and homologous recombination[5]. Topoisomerase I breaks one strand in duplex DNA, forming a covalent 3'-phosphotyrosine linkage, and guides the relaxation of DNA supercoils[6,7]. It then reseals the single-strand DNA break and releases a relaxed duplex DNA molecule. The camptothecins bind to the covalent topoisomerase I-DNA complex and prevent the religation of the broken single DNA strand, effectively trapping the 91 kDa protein on the DNA[4]. Such immobilized macromolecular adducts act as roadblocks to the progression of DNA replication and transcription complexes, causing double-strand DNA breaks and apoptosis[3]. Because cancer cells are growing rapidly, the camptothecins impact neoplastic cells more significantly than normal human tissues. Structural studies have established that the camptothecins stack into the duplex DNA, replacing the base pair adjacent to the covalent phosphotyrosine linkage[8,9]. Religation of the nicked DNA strand is prevented by increasing the distance between the 5'-hydroxyl and the 3'-phosphotyrosine linkage to >11 Å[8,9].

CPT-11 efficacy is severely limited by delayed diarrhea that accompanies treatment[10]. While an early cholinergic syndrome that generates diarrhea within hours can be successfully treated with atropine, the diarrhea that appears ~2-4 days later is significantly more debilitating and difficult to control[11]. CPT-11 undergoes a complex cycle of activation and metabolism that directly contributes to drug-induced diarrhea[11]. CPT-11 administered by intravenous injection can traffic throughout the body, but concentrates in the liver where it is activated to SN-38 by the human liver carboxylesterase hCE1. The SN-38 generated in the liver is conjugated in the liver to yield SN-38 glucuronide (SN-38G)[12]. SN-38G is excreted from the liver via the bile duct and into the intestines. Once in the intestines, however, SN-38G serves as a substrate for bacterial glucuronidase enzymes in the intestinal flora that remove the glucuronide moiety and produce the active SN-38[13]. SN-38 in the intestinal lumen produced in this manner contributes to epithelial cell death and the severe diarrhea that limits CPT-11 tolerance and efficacy. This effect has been partially reversed in rats using the relatively weak ($IC_{50}$=90 µM) β-glucuronidase inhibitor saccharic acid 1,4-lactone[14].

While broad-spectrum antibiotics have been used to eliminate enteric bacteria from the gastrointestinal tract prior to CPT-11 treatment[15], this approach has several drawbacks. First, intestinal flora play essential roles in carbohydrate metabolism, vitamin production, and the processing of bile acids, sterols and xenobiotics[16,17]. Thus, the partial or complete removal of gastrointestinal bacteria is non-ideal for patients already challenged by neoplastic growths and chemotherapy. Second, it is well established that the elimination of the symbiotic gastrointestinal flora from even healthy patients significantly increases the chances of infections by pathogenic bacteria, including enterohemorrhagic *E. coli* and *C. difficile*[18-24]. Third, bacterial antibiotic resistance is a human health crisis, and the unnecessary use of antimicrobials is a significant contributor to this problem[19]. For these reasons, we pursued the targeted inhibition of gastrointestinal bacterial glucuronidases rather than the broad-spectrum elimination of all enteric microflora.

Glucuronidases hydrolyze glucuronic acid sugar moieties in a variety of compounds[25]. The presence of glucuronidases in a range of bacteria is exploited in commonly-used water purity tests, in which the conversion of 4-methylumbelliferyl glucuronide (4-MUG) to 4-methylumbelliferone (4-MU) by glucuronidases is assayed to detect bacterial contamination[26]. Whereas relatively weak inhibitors of glucuronidase have been reported[27], no potent and/or selective inhibitors of the bacterial enzymes have been presented. Thus, there is a need for selective inhibitors of bacterial glucuronidase with a purpose of reducing the dose-limiting side effect and improving the efficacy of the CPT-11 anticancer drug.

SUMMARY OF THE INVENTION

The present invention relates to a compound that is effective as an inhibitor of glucuronidase activity.

The present invention relates to a compound for use with camptothecin-derived anticancer drugs. Use of a compound of the invention with an camptothecin-derived anticancer drug like CPT-11 for treating cancer reduces the dose-limiting side effects and improves the efficacy of CPT-11 (also called Irinotecan, and Camptosar®; Pfizer. In an aspect of the invention the compound is of formula (I) as described below, which are phenoxy thiophene sulfonamides. In another aspect of the invention, the compound may be a pyridine sulfonyl, benzene sulfonyl, thioophene sulfonyl, thiazole sulfonyl, thiophene carbonyl, and/or thiazole carbonyl. In still another aspect of the invention, the compound of formula (I), or a compound that is a pyridine sulfonyl, benzene sulfonyl, thioophene sulfonyl, thiazole sulfonyl, thiophene carbonyl, and/or thiazole carbonyl, is administered prior to, at the same time as or following administration of CPT-11. The present invention also relates to a method for synthesizing compounds for inhibiting glucuronidases. In an aspect of the invention the compound used of formula (I) as described below, which is a phenoxy thiophene sulfonamide. In another aspect of the invention the compound used may be a pyridine sulfonyl, benzene sulfonyl, thiophene sulfonyl, thiazole sulfonyl, thiophene carbonyl, and/or thiazole carbonyl.

The present invention also relates to a method for inhibiting glucuronidase in a subject in need thereof which comprises administering to the subject one or more compounds that inhibit glucuronidase. The present invention also relates to a method for inhibiting ∃ glucuronidases in a subject in need thereof which comprises administering to the subject one or more compounds that inhibit glucuronidase. In an aspect of the invention the compound used is of formula (I) as described below, which is a phenoxy thiophene sulfonamide. In another aspect of the invention the compound used may be a pyridine sulfonyl, benzene sulfonyl, thiophene sulfonyl, thiazole sulfonyl, thiophene carbonyl, and/or thiazole carbonyl.

In particular, the present invention relates to a compound of the formula (I):

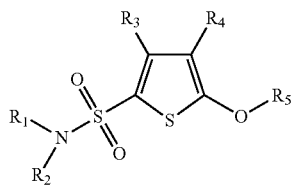

or a pharmaceutically acceptable salt thereof wherein
each of $R_1$ and $R_2$ is the same or different and is selected from H, naphthalene, naphthalene-($C_1$-$C_4$)alkyl, naphthalene-1-ylmethyl, naphthalene-1-ylethyl, naphthalene-1-ylpropyl 3-fluorobenzyl, 3-chlorobenzyl, 3-bromobenzyl, 3-iodobenzyl, 3-(trifluoromethyl)benzyl, 3-(trichloromethyl)benzyl, 3-(tribromomethyl)benzyl, 3-(triiodomethyl)benzyl, 3-($C_1$-$C_4$ alkyl)-benzyl, 3-methylbenzyl, 3-ethylbenzyl, 3-propylbenzyl, 3,5-dichlorobenzyl, 3,5-difluorobenzyl, 3,5,-dibromobenzyl, 3,5-diiodobenzyl, 3-chlorophenyl, 3-fluorophenyl, 3-bromophenyl, 3-iodophenyl, 3-($C_1$-$C_4$ alkyoxy)phenyl, 3-methoxyphenyl, 3-ethoxyphenyl, 3-propoxyphenyl, 4-methoxyphenyl, 4-($C_1$-$C_4$ alkyoxy)phenyl, 4-ethoxyphenyl, 4-propoxyphenyl, 2-chlorobenzyl, 3-chlorobenzyl, 4-chlorobenzyl, 2-fluorobenzyl, 3-fluorobenzyl, 4-fluorobenzyl, 2-bromobenzyl, 3-bromobenzyl, 4-bromobenzyl, 2-iodobenzyl, 3-iodobenzyl, 4-iodobenzyl, 3-($C_1$-$C_4$ alkyoxy)benzyl; 3-methoxybenzyl, 4-methoxybenzyl, 3-ethoxybenzyl, 4-ethoxybenzyl, 3-propoxybenzyl, 4-($C_1$-$C_4$ alkyoxy)phenyl and 4 propoxybenzyl;
each of $R_3$ and $R_4$ is the same or different and is selected from H, F, Cl, Br, and I, and $R_5$ is selected from 3-(R-1-yl)phenyl, and 4-(R-1-yl)phenyl, wherein R is selected from piperazin, 4-($C_1$-$C_4$ alkyl) piperazin, 4-methylpiperazin, 4-ethyl-piperazin, and 4-propylpiperazin.

The compounds of the invention are useful in eliminating the diarrhea associated with CPT-11 use for the treatment of cancer.

ABBREVIATIONS

Br=bromine
Cl=chlorine
CPT=camptothecin
DCM=Dichloromethane
DMEM=Dulbecco's Minimal Essential Media
DMF=Dimethylformamide
DMSO=Dimethylsulfoxide
DNA=deoxyribonucleic acid
F=fluorine
FPLC=fast performance liquid chromatography
H=hydrogen
HEPES=(4-(2-hydroxyethyl)-1-piperazineethanesulfonic acid
I=iodine
kDal=kilodalton
MHz=megahertz
mmol=millimole
µMol=micromolar
NMR=nuclear magnetic resonance
Nm=nanometer
OD=optical density
PMB=p-methoxybenzyl
PMSF=phenylmethylsulfonyl fluoride
ppm=parts per million
SDS-PAGE=sodium dodecyl sulfate polyacrylamide gel electrophoresis
TBAI=tetrabutylammonium iodide
TFA=Trifluoroacetic acid

DETAILED DESCRIPTION OF THE INVENTION

For purposes of the following detailed description, it is to be understood that the invention may assume various alternative variations and step sequences, except where expressly specified to the contrary. Moreover, other than in any operating examples, or where otherwise indicated, all numbers expressing, for example, quantities of ingredients used in the specification and claims are to be understood as being modified in all instances by the term "about". Accordingly, unless indicated to the contrary, the numerical parameters set forth in the following specification and attached claims are approximations that may vary depending upon the desired properties to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard variation found in their respective testing measurements.

Also, it should be understood that any numerical range recited herein is intended to include all sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of equal to or less than 10.

In this application, the use of the singular includes the plural and plural encompasses singular, unless specifically stated otherwise. In addition, in this application, the use of "or" means "and/or" unless specifically stated otherwise, even though "and/or" may be explicitly used in certain instances.

In the present invention, 76 phenoxythiophene sulfonamides from a 35,000 compound diversity set library were tested for their ability to inhibit the bacterial enzyme β-glucuronidase. The structures and inhibitory activity of the compounds are shown in Table 1.

In the present invention, 18 analogs of BRITE-355252 were synthesized and tested to initially explore the structural relationship these compounds display towards inhibition of β-glucuronidase. The structures and inhibitory activity of the 18 analogs of BRITE-355252 are shown in Table 2.

Compounds of formula (I)

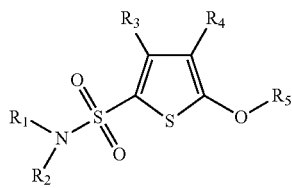

wherein $R_1$, $R_2$, $R_3$, $R_4$ and $R_5$ are as defined above can be prepared by a process comprising the steps of (a) reacting a halo thiophene-sulfonyl halo and $R_1$—N—$H_2$, to form a resultant N-monoprotected thiophene sulfonamide having a first N-protecting group comprising $R_1$, (b) reacting the resultant N-monoprotected amide with $R_2$—N-halo and a catalyst in a base, to form a resultant N,N-diprotected thiophene sulfonamide having also a second N-protecting group comprising $R_2$, (c) reacting the resultant N,N-diprotected thiophene sulfonamide with $Cs_2CO_3$ and phenol group substituted by R; wherein R is selected from piperazin, 4-($C_1$-$C_4$ alkyl) piperazin, 4-methylpiperazin, 4-ethyl-piperazin, and 4-propylpiperazin, in a solvent, and then removing the solvent, to obtain a resultant N,N-diprotected phenoxy thiophene sulfonamide, and (d) reacting the resultant N,N-diprotected phenoxy thiophene sulfonamide with a deprotecting agent that is selective for deprotecting the second N-protecting group, thereby removing the second N-protecting group, and forming a N-monoprotected phenoxy thiophene sulfonamide.

The halogen atom of the halo thiophene-sulfonyl halo compound is selected from bromine, chlorine, fluorine and iodine.

Any base that will in combination with the N-monoprotected amide with $R_2$—N-halo and a catalyst result in a N,N-diprotected thiophene sulfonamide can be used.

Non-limiting examples of bases that can be used are $Et_3N$, $Na_2CO_3$, $K_2CO_3$ and NaH and any base described in the examples.

In an embodiment of the invention the halo thiophene-sulfonyl halo is dichlorothiophene-sulfonyl chloride and $R1$-N—$H_2$ is naphthylmethylamine. These groups are mixed and cooled to form a N-monoprotected thiophene sulfonamide, having a first N-protecting group that comprises naphthylmethyl.

In an embodiment of the invention the resultant N-monoprotected thiophene sulfonamide, is mixed with methoxybenzyl bromide and a catalyst that can be used in a Finkelstein reaction in sodium hydride, and cooled thereby forming a N,N-diprotected thiophene sulfonamide having also a second N-protecting group that comprises methoxybenzyl, and the resultant N,N-monoprotected thiophene sulfonamide, and $Cs_2CO_3$ and tea-butyl(hydroxyphenyl)piperazine-carboxylate in a solvent, are mixed and heated. The solvent is then removed to obtain a resultant N,N-diprotected phenoxy thiophene sulfonamide.

In an embodiment of the invention the resultant N,N-diprotected phenoxy thiophene sulfonamide is mixed with a deprotecting agent that is selective for deprotecting the second N-protecting group, thereby removing the methoxy benzyl that is the second N-protecting group, and thereby forming a N-alkyl or N-aryl phenoxy thiophene sulfonamide.

Examples of non-limiting embodiments of the invention are where: the dichlorothiophene-sulfonyl chloride is 4,5-dichlorothiophene-2-sulfonyl chloride; the naphthylmethylamine is 1-naphthylmethylamine; the methoxybenzyl bromide is 4-methoxybenzyl bromide; the catalyst is tetrabutylammonium iodide; the butyl(hydroxyphenyl)piperazine-carboxylate is tert-butyl-4-(3-hydroxyphenyl)piperazine-1-carboxylate; the solvent is dimethyl formamide and/or the selective deprotecting agent comprises dichloromethane and trifluoroacetic acid; or a combination thereof.

In addition to dimethyl formamide, non-limiting examples of solvents that can be used are DMSO and dioxane and the solvents described in the examples.

The following reaction Scheme 1 illustrates the preparation of compounds within the scope of the present invention:

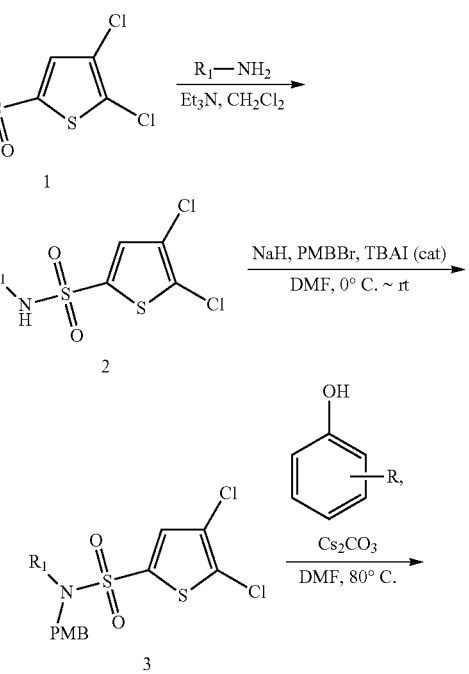

-continued

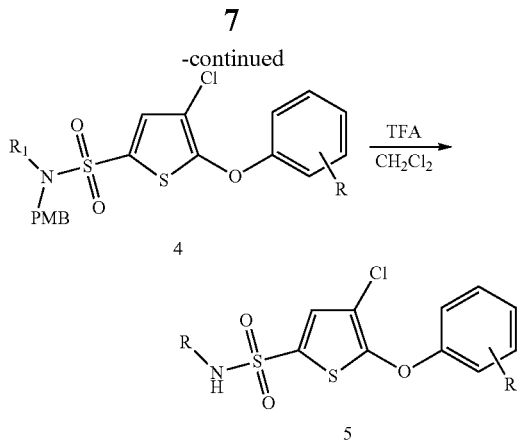

Scheme 1 refers to the preparation of compounds of formula I. Referring to Scheme 1, compounds of the formula I are prepared by reacting commercially available 4,5-dichlorothiophene-2-sulfonyl chloride 1 with an amine to generate dichlorothiophene sulfonamide 2. PMB (p-methoxybenzyl) protected 4,5-dichlorothiophene sulfonamide 3 is generated by reacting compound 2 with NaH in DMF, pmethoxybenzyl bromide and a catalytic amount of TBAI. Nucleophilic displacement of the C-5 chlorine with a phenol in the presence of $Cs_2CO_3$ produce N,N-diprotected 5-(3-phenoxy)-thiophene-2-sulfonamide 3. In the final step, the protecting group is removed using TFA in DCM (1:1) to give the desired compound.

The term "pharmaceutically acceptable salts" refers to the non-toxic, inorganic and organic acid addition salts and base addition salts of compounds of the present invention.

Such conventional non-toxic salts include those derived from inorganic acids such as hydrochloric, hydrobromic, sulfuric, sulfamic, phosphoric, and nitric acid; and the salts prepared from organic acids such as acetic, propionic, succinic, glycolic, stearic, lactic, malic, tartaric, citric, ascorbic, palmoic, maleic, hydroxy-maleic, phenylacetic, glutamic, benzoic, salicylic, sulfanilic, 2-acetoxybenzoic, fumaric, toluenesulfonic, methanesulfonic, ethane disulfonic, oxalic, and isethionic acid. Pharmaceutically acceptable salts from amino acids may also be used. Such as salts of arginine and lysine.

Pharmaceutically acceptable salts may be synthesized from the parent compound which contains a basic or acidic moiety by conventional chemical methods. Generally, such salts may be prepared by reacting the free acid or base forms of these compounds with a stoichiometric amount of the appropriate base or acid in water or in an organic solvent, or in a mixture of the two.

As used herein, the terms "treatment" and "therapy" and the like refer to alleviate, slow the progression, prophylaxis, or attenuation of existing disease.

As used herein, the terms "inhibit," "inhibiting," and the like means that the activity of glucuronidase is reduced.

As used herein, the term "subject" means an animal or human.

The pharmaceutical compositions of this invention comprise one or more compounds that inhibit glucuronidase and one or more pharmaceutically acceptable carriers, diluents, and excipients.

Pharmaceutical compositions of the present invention may be in a form suitable for use in this invention for examples compositions may be formulated for i) oral use, for example, aqueous or oily suspensions, dispersible powders or granules, elixirs, emulsions, hard or soft capsules, lozenges, syrups, tablets or trouches; ii) parenteral administration, for example, sterile aqueous or oily solution for intravenous, subcutaneous, intraperitoneal, or intramuscular; iii) delivered intracerebrally or iv) topical administration, for example, a suppository or ointment.

As used herein the term "pharmaceutically acceptable" is meant that the carrier, diluent, excipients, and/or salt must be compatible with the other ingredients of the formulation including the active ingredient(s), and not deleterious to the recipient thereof.

"Pharmaceutically acceptable" also means that the compositions, or dosage forms are within the scope of sound medical judgment, suitable for use for an animal or human without excessive toxicity, irritation, allergic response, or other problem or complication, commensurate with a reasonable benefit/risk ratio.

A compound can also be used in the manufacture of a medicament. This medicament can be used for the purposes described herein.

The compositions or medicaments normally contain about 1 to 99%, for example, about 5 to 70%, or from about 5 to about 30% by weight of the compound or its pharmaceutically acceptable salt. The amount of the compound or its pharmaceutically acceptable salt in the composition will depend on the type of dosage form and the pharmaceutically acceptable excipients used to prepare it.

The dose of the compounds of this invention, which is to be administered, can cover a wide range. The dose to be administered daily is to be selected to suit the desired effect. Actual dosage levels of the active ingredients in the pharmaceutical compositions of this invention may be varied so as to obtain an amount of the active ingredient, which is effective to achieve the desired therapeutic response for a particular patient, composition, and mode of administration without causing undue side effects or being toxic to the patient.

The selected dosage level will depend upon a variety of factors, including the activity of the particular compound of the present invention employed, the route of administration, the time of administration, the rate of excretion of the particular compound being employed, the duration of the treatment, other drugs, compounds and/or materials used in combination with the particular compounds employed, the age, sex, weight, condition, general health and prior medical history of the patient being treated, and like factors well known in the medical arts.

As used herein, "effective amount" and the like means the amount of the compound or composition necessary to achieve a therapeutic effect.

An effective amount of the therapeutic compound necessary to achieve a therapeutic effect may vary according to factors such as the age, sex, and weight of the subject. Dosage regimens can be adjusted to provide the optimum therapeutic response. For example, several divided doses may be administered daily or the dose may be proportionally reduced as indicated by the exigencies of the therapeutic situation.

Compounds of the invention can be formulated into compositions that can be administered to a subject in need of a glucuronidase inhibitor.

The compounds or compositions thereof are used for inhibition of glucuronidase.

The compounds or compositions thereof are used in methods for treating a subject in need of a glucuronidase inhibitor. The compounds or compositions are administered in an amount that is effective to inhibit the glucuronidase. In some embodiments of the invention it is ∃ glucuronidase or bacterial ∃ glucuronidase that is inhibited.

The compounds or compositions can be administered prior to, concurrently with or after administration of a camptothecin-derived anticancer agent such as CPT-11. Administration of the compounds or compositions may result in certain benefits such as decreasing the dose of the anticancer drug, increasing the tolerance of the anticancer drug and alleviating side effects from the use of the anticancer drug. Side effects include gastrointestinal side effects.

The invention is further understood by reference to the following Examples, which are intended to be purely exemplary of the invention. The present invention is not limited in scope by the exemplified embodiments, which are intended as illustrations of single aspects of the invention only. Any methods that are functionally equivalent to those described in the Examples are within the scope of the invention. Various modifications of the invention in addition to those described herein will become apparent to those skilled in the art from the foregoing description. Such modifications fall within the scope of the appended claims.

Example 1

β-Glucuronidase Activity Assay

Expression and Purification of *E. coli* β-Glucuronidase

The full-length *E. coli* β-glucuronidase gene was obtained from bacterial genomic DNA and was cloned into the pET-28a expression plasmid (Novagen) with an N-terminal 6x-Histidine tag. BL21-DE3 competent cells were transformed with the expression plasmid and grown in the presence of kanamycin (25 ug/ml) in LB medium with vigorous shaking at 37° C. until an $OD_{600}$ of 0.6 was attained. The expression was induced with the addition of 0.3 mM isopropyl-1-thio-D-galactopyranoside (IPTG) and further incubated at 37° C. for 4 hours. Cells were collected by centrifugation at 4500×g for 20 min at 4° C. Cell pellets were resuspended in Buffer A (20 mM Potassium Phosphate, pH 7.4, 25 mM Imidazole, 500 mM NaCl), along with PMSF (2 μL/mL from 100 mM stock) and 0.05 μL/mL of protease inhibitors containing 1 mg/mL of aprotinin and leupeptin. Resuspended cells were sonicated and centrifuged at 14,500×g for 30 min to clarify the lysate. The cell lysate was flowed over a pre-formed Ni-NTA His-Trap gravity column and washed with Buffer A. The Ni-bound protein was eluted with Buffer B (20 mM Potassium Phosphate, pH 7.4, 500 mM Imidazole, 500 mM NaCl). Collected fractions were then tested for initial purity by SDS-PAGE. Relatively pure (~85%) fractions were combined and loaded into the Äktaxpress FPLC system and passed over a HiLoad™ 16/60 Superdex™ 200 gel filtration column. The protein was eluted into 20 mM HEPES, pH 7.4, and 50 mM NaCl for crystallization and activity assays. Two milliliter fractions were collected based on highest ultraviolet absorbance at 280 nm. Fractions were analyzed by SDS-PAGE (which indicated >95% purity), combined, and concentrated to 10 mg/mL for long-term storage at −80° C.

β-Glucuronidase Assay

The β-glucuronidase assay was performed by the addition of 0.5 μl of compound (or DMSO) to the well of a black 384-well plate followed by the addition of 30 μl of diluted β-glucuronidase enzyme. The enzyme was diluted in assay buffer (50 mM HEPES, pH 7.4) plus 0.0166% Triton X-100 for a final enzyme concentration of 50 pM and final detergent concentration of 0.01%. After a 15 minute incubation at room temperature (23° C.), 20 ul of substrate, 4-Methylumbelliferyl β-D-glucuronide hydrate (4MUG) diluted into assay buffer, was added to the reaction for a final concentration of 125 uM. β-glucuronidase hydrolyzes the non-fluorescent 4MUG resulting in a fluorescent product, 4-methylumbelliferyl. After a 30 minute incubation at room temperature, the reaction was stopped by the addition of 20 ul 1 M $Na_2CO_3$. The fluorescence (in relative fluorescence units, RFU) was measured using a 355 nm excitation filter and 460 nm emission filter using a Victor V (Perkin Elmer) plate reader. Minimum (min) controls were performed using reactions with no enzyme. Maximum (max) controls were performed using no compound. 1% DMSO was maintained in all reactions. Percent inhibition was calculated using RFU data by the following formula: [1−(assay readout−average of min)/(Average of Max−Average of Min)]×100. The known β-glucuronidase inhibitor, D-Glucaric acid-1,4-lactone monohydrate, was used to validate the assay and serve as a positive control. $IC_{50}$ value was defined as the concentration of inhibitor calculated to inhibit 50% of the assay signal based on a serial dilution of compound. Values were calculated using either a four or three-parameter dose response (variable slope) equation in GraphPad Prism™ or ActivityBase™. For the $IC_{50}$ determinations, serial dilutions of compounds were performed in 100% DMSO with a two-fold dilution scheme resulting in 10 concentrations of compound. These results are shown in Tables 1 and 2.

Example 2

Preparation of Analogs of BRITE-355252

General Procedures for the Preparation of Analogs of BRITE-355252

All solvents and reagents were obtained from commercial sources and used without further purification unless otherwise stated. All reactions were performed in oven-dried glassware (either in RB flasks or 20 ml vials equipped with septa) under an atmosphere of nitrogen and the progress of reactions was monitored by thin-layer chromatography and LC-MS. Analytical thin-layer chromatography was performed on precoated 250 μm layer thickness silica gel 60 $F_{254}$ plates (EMD Chemicals Inc.). Visualization was performed by ultraviolet light and/or by staining with phosphomolybdic acid (PMA) or p-anisaldehyde. All the silica gel chromatography purifications were carried out by using Combiflash® Rf (Teledyne Isco) and CombiFlash® Companion® (Teledyne Isco) either with EtOAc/hexane or MeOH/$CH_2Cl_2$ mixtures as the eluants. Melting points were measured on a MEL-TEMP® capillary melting point apparatus and are uncorrected. Proton nuclear magnetic resonance ($^1$H NMR) spectra and carbon nuclear magnetic resonance ($^{13}$C NMR) spectra were recorded on a Varian VNMRS-500 (500 MHz) spectrometer. Chemical shifts (δ) for proton are reported in parts per million (ppm) downfield from tetramethylsilane and are referenced to it (TMS 0.0 ppm). Coupling constants (J) are reported in Hertz. Multiplicities are reported using the following abbreviations: br=broad; s=singlet; d=doublet; t=triplet; q=quartet; m=multiplet. Chemical shifts (δ) for carbon are reported in parts per million (ppm) downfield from tetramethylsilane and are referenced to residual solvent peaks: carbon ($CDCl_3$ 77.0 ppm). Mass spectra were recorded on an Agilent 1200 Series LC/MS instrument equipped with a XTerra® MS (C-18, 3.5 μm) 3.0×100 mm column.

Representative Procedure for the Preparation of 4,5-dichloro-N (aryl/alkyl)thiophene-2-sulfonamides To a solution of 4,5-dichlorothiophene-2-sulfonyl chloride (1.000 g, 4.002 mmol) in anhydrous $CH_2Cl_2$ (20 mL) was added 1-naphthylmethylamine (0.630 g, 4.007 mmol) followed by $Et_3N$ (0.84 mL, 6.027 mmol) and stirred at room temperature for 2 h. The reaction mixture was diluted with water (20 mL) and extracted with $CH_2Cl_2$ (100 mL), washed with brine, dried ($Na_2SO_4$) and concentrated under vacuo. The residue was purified by recrystallization from $CH_2Cl_2$-hexane to afford the pure 4,5-dichloro-N-(naphthalen-1-ylmethyl)thiophene-2-sulfonamide (1.350 g, 91%) as a white crystalline product.

Representative Procedure for the PMB Protection of 4,5-dichloro-N (aryl/alkyl)thiophene-2-sulfonamides Sodium hydride (0.081 g, 3.375 mmol) was slowly added in portions to a solution of 4,5-dichloro-N-(naphthalen-1-ylmethyl)thiophene-2-sulfonamide (1.250 g, 3.358 mmol) in anhydrous DMF (10 mL) at 0° C. and stirred for 15 min. Then, 4-methoxybenzyl bromide (PMBBr) (0.675 g, 3.357 mmol), and a catalytic amount of TBAI (0.030 g, 0.081 mmol) were added at 0° C., and allowed to stir at room temperature for 2 h. After completion of the reaction, it was quenched by slow addition of water (5 mL) and extracted with EtOAc (100 mL), washed with water and brine, dried ($Na_2SO_4$), concentrated under vacuo and the residue purified by flash silica gel column chromatography (Combiflash® Rf) using EtOAc-hexane (1:9) as eluant to afford 4,5-dichloro-N-(4-methoxybenzyl)-N-(naphthalen-1-ylmethyl)thiophene-2-sulfonamide (1.500 g, 91%) as a white solid.

Representative Procedure for the Coupling of Phenols with PMB Protected 4,5-dichloro-N-(aryl/alkyl)thiophene-2-sulfonamides A mixture of 4,5-dichloro-N-(4-methoxybenzyl)-N-(naphthalen-1-ylmethyl)thiophene-2-sulfonamide (0.100 g, 0.203 mmol), tert-butyl 4-(3-hydroxyphenyl)piperazine-1-carboxylate (0.068 g, 0.244 mmol) and $Cs_2CO_3$ (0.099 g, 0.304 mmol) in anhydrous DMF (2 mL) was heated at 80° C. for 2.5 h. The solvent was removed under vacuo and the residue was purified by Combiflash® Rf (Isco) using EtOAc-hexanes (1:9) to obtain a white solid (0.140 g, 94%).

Representative Procedure for the Deprotection PMB Group

To a solution of tert-butyl 4-(3-(3-chloro-5-(N-(4-methoxybenzyl)-N-(naphthalen-1-ylmethyl)sulfamoyl)thiophen-2-yloxy)phenyl)piperazine-1-carboxylate (0.085 g, 0.116 mmol) in anhydrous $CH_2Cl_2$ (2 mL) was added TFA (2 mL) and stirred at room temperature for 3 h. The solvent mixture was removed under vacuo and the residue was re-dissolved in $CH_2Cl_2$ (20 mL), washed with aqueous sat. $NaHCO_3$ followed by brine, dried ($Na_2SO_4$), and concentrated under vacuo.

BRITE-355252

4-Chloro-N-(naphthalen-1-ylmethyl)-5-(3-(piperazin-1-yl)phenoxy)thiophene-2-sulfonamide The crude product was purified by flash silica gel column chromatography using MeOH—$CH_2Cl_2$ (1:9) to afford a light orange solid (0.055 g, 92%). $^1$H NMR (500 MHz, DMSO-$d_6$): δ(ppm): 2.81 (t, 4H, J=5.0 Hz), 3.09 (t, 4H, J=5.0 Hz), 4.56 (s, 2H), 6.43 (dd, 1H, J=2.0, 8.0 Hz), 6.75 (t, 1H, J=2.5 Hz), 6.83 (dd, 1H, J=2.5, 8.0 Hz), 7.26 (t, 1H, J=8.0 Hz), 7.43-7.48 (m, 3H), 7.54-7.58 (m, 2H), 7.87 (dd, 1H, J=1.5, 7.5 Hz), 7.93-7.96 (m, 1H), 8.06-8.09 (m, 1H). APCI/ESI MS: m/z 513.9 $[M+H]^+$

BRITE-492796

4-Chloro-N-methyl-N-(naphthalen-1-ylmethyl)-5-(3-(piperazin-1-yl)phenoxy)thiophene-2-sulfonamide The product was prepared in 89%% yield; White solid, mp: 144-146° C.;
$^1$H NMR (500 MHz, DMSO-$d_6$): δ (ppm): 2.55 (s, 3H), 2.86 (t, 4H, J=4.5 Hz), 3.14 (t, 4H, J=4.5 Hz), 4.63 (s, 2H), 6.62-6.66 (m, 1H), 6.84-6.88 (m, 2H), 7.30 (t, 1H, J=8.0 Hz), 7.48-7.62 (m, 4H), 7.91 (s, 1H), 7.94 (d, 1H, J=8.0 Hz), 7.98 (d, 1H, J=9.0 Hz), 8.29 (d, 1H, J=8.0 Hz). APCI/ESI MS m/z 527.9 $[M+H]^+$

BRITE-492794

4-Chloro-5-(3-(4-methylpiperazin-1-yl)phenoxy)-N-(naphthalen-1-ylmethyl)thiophene-2-sulfonamide The product was prepared in 89%% yield; White solid, mp: 156-158° C.; $^1$H NMR (500 MHz, DMSO-$d_6$): δ (ppm): 2.21 (s, 3H), 2.43 (t, 4H, J=5.0 Hz), 3.17 (t, 4H, J=5.0 Hz), 4.55 (d, 2H, J=4.5 Hz), 6.44 (dd, 1H, J=2.0, 8.0 Hz), 6.78 (t, 1H, J=2.0 Hz), 6.84 (dd, 1H, J=2.0, 8.0 Hz), 7.27 (t, 1H, J=8.0 Hz), 7.43-7.48 (m, 3H), 7.53-7.58 (m, 2H), 7.88 (dd, 1H, J=1.5, 7.5 Hz), 7.93-7.97 (m, 1H), 8.05-8.09 (m, 1H), 8.52 (t, 1H, J=4.5 Hz, NH). APCI/ESI MS Im/z 527.9 $[M+H]^+$

BRITE-492809

4-Chloro-N-(3-fluorobenzyl)-5-(3-(piperazin-1-yl)phenoxy)thiophene-2-sulfonamide The product was prepared in 75% yield; White solid, mp: 86-88° C. (decomposed); $^1$H NMR (500 MHz, DMSO-$d_6$): δ (ppm): 3.06 (t, 4H, J=5.0 Hz), 3.20 (t, 4H, J=5.0 Hz), 4.23 (s, 2H), 6.54 (dd, 1H, J=2.5, 8.0 Hz), 6.67 (t, 1H, J=2.5 Hz), 6.77 (dd, 1H, J=2.5, 8.0 Hz), 6.95-7.02 (m, 2H), 7.04 (d, 1H, J=7.0 Hz), 7.23-7.32 (m, 2H), 7.33 (s, 1H).
APCI/ESI MS m/z481.9 $[M+H]^+$

BRITE-354873

4-Chloro-5-(3-(piperazin-1-yl)phenoxy)-N-(3-(trifluoromethyl)benzyl)thiophene-2-sulfonamide The product was prepared in 71% yield; White solid, mp: 58-60° C. (decomposed): $^1$H NMR (500 MHz, CDCl$_3$): δ (ppm): 3.03 (t, 4H, J=5.0 Hz), 3.17 (t, 4H, J=5.0 Hz), 4.29 (s, 2H), 6.53 (dd, 1H, J=2.5, 8.0 Hz), 6.66 (t, 1H, J=2.5 Hz), 6.76 (dd, 1H, J=2.5, 8.0 Hz), 7.22-7.25 (m, 1H), 7.31 (s, 1H), 7.43-7.50 (m, 3H), 7.56 (d, 1H, J=7.0 Hz).
APCI/ESI MS m/z 531.9 $[M+H]^+$

BRITE-492808

4-Chloro-N-(3-methylbenzyl)-5-(3-(piperazin-1-yl)phenoxy)thiophene-2-sulfonamide The product was prepared in 71% yield; White solid, mp: 122-124° C.: $^1$H NMR (500 MHz, CDCl$_3$): δ (ppm): 2.33 (s, 3H), 3.03 (t, 4H, J=5.0 Hz), 3.17 (t, 4H, J=5.0 Hz), 4.20 (s, 2H), 6.52 (dd, 1H, J=2.5, 8.0 Hz), 6.66 (t, 1H, J=2.5 Hz), 6.76 (dd, 1H, J=2.5, 8.0 Hz), 7.02 (d, 1H, J=8.0 Hz), 7.04 (s, 1H), 7.11 (d, 1H, J=7.5 Hz), 7.20 (d, 1H, J=8.0 Hz), 7.23 (d, 1H, J=8.0 Hz), 7.32 (s, 1H). APCI ESI-MS m/z 477.9 [M+H]$^+$

BRITE-492807

4-Chloro-N-(3,5-dichlorobenzyl)-5-(3-(piperazin-1-yl)phenoxy)thiophene-2-sulfonamide The product was prepared in 89% yield; Yellowish syrup: $^1$H NMR (500 MHz, CDCl$_3$): δ (ppm): 3.06 (t, 4H, J=5.0 Hz), 3.20 (t, 4H, J=5.0 Hz), 4.19 (s, 2H), 6.56 (dd, 1H, J=1.5, 8.0 Hz), 6.68 (s, 1H), 6.77 (dd, 1H, J=1.5, 8.0 Hz), 7.14 (d, 2H, J=0.5 Hz), 7.24-7.29 (m, 2H), 7.31 (s, 1H). APCI/ESI MS m/z 531.8 [M+H]$^+$

BRITE-354909

4-Chloro-N-(4-methoxyphenyl)-5-(3-(piperazin-1-yl)phenoxy)thiophene-2-sulfonamide The product was prepared in 89% yield; White solid, mp: 118-120° C.: $^1$H NMR (500 MHz, CDCl$_3$+CD$_3$OD): δ (ppm): 3.02 (t, 4H, J=5.0 Hz), 3.16 (t, 4H, J=5.0 Hz), 3.79 (s, 3H), 6.48 (dd, 1H, J=1.5, 8.0 Hz), 6.60 (t, 1H, J=1.5 Hz), 6.74 (dd, 1H, J=2.0, 8.5 Hz), 6.81-6.85 (m, 2H), 7.05-7.09 (m, 2H), 7.18 (s, 1H), 7.22 (t, 1H, J=8.0 Hz). APCI/ESI MS m/z 479.9 [M+H]$^+$

BRITE-492806

4-Chloro-N-(naphthalen-1-ylmethyl)-5-(4-(piperazin-1-yl)phenoxy)thiophene-2-sulfonamide The product was prepared in 97% yield; Light orange solid, mp: 156-158° C.: $^1$H NMR (500 MHz, CDCl$_3$): δ (ppm): 3.04-3.07 (m, 4H), 3.13-3.16 (m, 4H), 4.65 (s, 2H), 6.89-6.92 (m, 2H), 7.02-7.05 (m, 2H), 7.32 (s, 1H), 7.37-7.42 (m, 2H), 7.52-7.55 (m, 2H), 7.83 (dd, 1H, J=2.0, 7.0 Hz), 7.86-7.89 (m, 1H), 7.92-7.94 (m, 1H).
APCI/ESI MS m/z 514.0 [M+H]$^+$

BRITE-492805

4-Chloro-N-(2-chlorobenzyl)-5-(3-(piperazin-1-yl)phenoxy)thiophene-2-sulfonamide The product was prepared in 83% yield; Light orange solid, mp: 99-101° C.: $^1$H NMR (500 MHz, CDCl$_3$): δ (ppm): 3.02-3.04 (m, 4H), 3.15-3.18 (m, 4H), 4.35 (s, 2H), 6.49 (dd, 1H, J=2.0, 8.0 Hz), 6.64 (t, 1H, J=2.0 Hz), 6.75 (dd, 1H, J=2.5, 8.5 Hz), 7.20 (s, 1H), 7.22 (d, 1H, J=0.5 Hz), 7.24 (s, 1H), 7.30 (s, 1H), 7.32-7.35 (m, 2H).
APCI/ESI MS m/z 497.9 [M+H]$^+$

BRITE-355123

4-Chloro-N-(3-chlorobenzyl)-5-(3-(piperazin-1-yl)phenoxy)thiophene-2-sulfonamide The product was prepared in 85% yield; White solid, mp: 123-125° C.: $^1$H NMR (500 MHz, CDCl$_3$): δ (ppm): 3.01-3.04 (m, 4H), 3.15-3.18 (m, 4H), 4.21 (s, 2H), 6.54 (dd, 1H, J=2.5, 8.0 Hz), 6.67 (t, 1H, J=2.5 Hz), 6.77 (dd, 1H, J=2.5, 8.0 Hz), 7.13-7.16 (m, 1H), 7.21-7.30 (m, 4H), 7.32 (s, 1H).
APCI/ESI MS m/z 497.9 [M+H]$^+$

BRITE-492802

4-Chloro-N-(4-chlorobenzyl)-5-(3-(piperazin-1-yl)phenoxy)thiophene-2-sulfonamide The product was prepared in 78% yield; Light orange solid, mp: 118-120° C.: $^1$H NMR (500 MHz, CDCl$_3$): δ (ppm): 3.01-3.04 (m, 4H), 3.15-3.18 (m, 4H), 4.20 (s, 2H), 6.53 (ddd, 1H, J=0.5, 2.0, 8.0 Hz), 6.67 (t, 1H, J=2.0 Hz), 6.77 (dd, 1H, J=2.0, 8.0 Hz), 7.18-7.21 (m, 2H), 7.22 (s, 1H), 7.29-7.32 (m, 2H), 7.34 (s, 1H).
APCI/ESI MS m/z 497.9 [M+H]$^+$

BRITE-492803

4-Chloro-N-(4-methoxybenzyl)-5-(3-(piperazin-1-yl)phenoxy)thiophene-2-sulfonamide The product was prepared in 48% yield; White solid, mp: 106-108° C.: $^1$H NMR (500 MHz, CDCl$_3$): δ (ppm): 2.97 (t, 4H, J=5.0 Hz), 3.12 (t, 4H, J=5.0 Hz), 3.77 (s, 3H), 4.14 (s, 2H), 6.51 (dd, 1H, J=2.0, 8.0 Hz), 6.64 (t, 1H, J=2.0 Hz), 6.73 (dd, 1H, J=2.0, 8.0 Hz), 6.82 (d, 2H, J=8.5 Hz), 7.14 (d, 2H, J=8.5 Hz), 7.23 (t, 1H, J=8.5 Hz), 7.28 (s, 1H). APCI/ESI MS m/z 494.0 [M+H]$^+$

BRITE-355227

4-Chloro-N-(3-methoxybenzyl)-5-(3-(piperazin-1-yl)phenoxy)thiophene-2-sulfonamide The product was prepared in 31% yield; White solid, mp: 60-62° C.: $^1$H NMR (500 MHz, CDCl$_3$): δ (ppm): 2.97 (t, 4H, J=5.0 Hz), 3.12 (t, 4H, J=5.0 Hz), 3.76 (s, 3H), 4.18 (s, 2H), 6.52 (dd, 1H, J=2.0, 8.0 Hz), 6.64 (t, 1H, J=2.0 Hz), 6.73 (dd, 1H, J=2.0, 8.5 Hz), 6.76 (s, 1H), 6.78-6.83 (m, 2H), 7.22 (ABq, 2H, J=8.5 Hz), 7.28 (s, 1H). APCI/ESI MS m/z 494.1 [M+H]$^+$

BRITE-492800

4-Chloro-N-(3-chlorophenyl)-5-(3-(piperazin-1-yl)phenoxy)thiophene-2-sulfonamide The product was prepared in 78% yield; White solid, mp: 154-156° C.: $^1$H NMR (500 MHz, CDCl$_3$): δ (ppm): 3.17 (t, 4H, J=5.0 Hz), 3.28 (t, 4H, J=5.0 Hz), 6.49 (dd, 1H, J=2.0, 8.0 Hz), 6.74 (s, 1H), 6.78 (d, 1H, J=7.5 Hz), 6.83 (dd, 1H, J=2.0, 8.0 Hz), 6.86 (dd, 1H, J=1.0, 7.5 Hz), 6.96 (s, 1H), 7.10 (t, 1H, J=8.0 Hz), 7.23 (s, 1H), 7.26 (t, 1H, J=8.0 Hz), 8.34 (br s, 1H, NH). APCI/ESIMS m/z 484.0 [M+H]$^+$

BRITE-492799

4-Chloro-N-(3-methoxyphenyl)-5-(3-(piperazin-1-yl)phenoxy)thiophene-2-sulfonamide The product was prepared in 78% yield; White solid, mp: 180-182° C.: $^1$H NMR (500 MHz, CDCl$_3$): δ (ppm): 3.03 (t, 4H, J=5.0 Hz), 3.14 (t, 4H, J=5.0 Hz), 3.78 (s, 3H), 6.47 (dd, 1H, J=2.0, 8.0 Hz), 6.59 (t, 1H, J=2.0 Hz), 6.65-6.68 (m, 1H), 6.71-6.76 (m, 3H), 7.18-7.23 (m, 2H), 7.27 (s, 1H).
APCI/ESI MS m/z 480.0 [M+H]$^+$

BRITE-492798

4-Chloro-5-(3-(piperazin-1-yl)phenoxy)thiophene-2-sulfonamide

To a solution of tert-butyl 4-(3-(5-(N,N-bis(4-methoxybenzyl)sulfamoyl)-3-chlorothiophen-2-yloxy)phenyl)piperazine-1-carboxylate (0.430 g, 0.602 mmol) in anhydrous $CH_2Cl_2$ (0.5 mL) was added TFA (4.5 mL) and stirred at room temperature for 4 h. The solvent mixture was removed under vacuo and the residue was re-dissolved in $CH_2Cl_2$ (30 mL), washed with aqueous sat. $NaHCO_3$ followed by brine, dried ($Na_2SO_4$), and concentrated under vacuo. The residue was purified by Combiflash® Rf (Isco) using MeOH—$CH_2Cl_2$ (1:5) to give a white solid (0.180 g, 80%). $^1H$ NMR (500 MHz, $CD_3OD$): δ (ppm): 3.02-3.05 (m, 4H), 3.19-3.22 (m, 4H), 6.56 (dd, 1H, J=2.0, 8.0 Hz), 6.73 (t, 1H, J=2.0 Hz), 6.84 (dd, 1H, J=2.0, 8.5 Hz), 7.27 (t, 1H, J=8.5 Hz), 7.40 (s, 1H).
APCI/ESI MS m/z 374.0 $[M+H]^+$

BRITE-492797

N-(Naphthalen-1-ylmethyl)-5-(3-(piperazin-1-yl)phenoxy)thiophene-2-sulfonamide The product was prepared in 87% yield; Light orange solid, mp: 65-67° C.: $^1H$ NMR (500 MHz, $CDCl_3$): δ (ppm): 2.92 (t, 4H, J=5.0 Hz), 3.08 (t, 4H, J=5.0 Hz), 4.62 (s, 2H), 6.43 (d, 1H, J=4.5 Hz), 6.56-6.60 (m, 1H), 6.65 (t, 1H, J=2.5 Hz), 6.71 (dd, 1H, J=2.0, 8.5 Hz), 7.23 (t, 1H, J=8.5 Hz), 7.37 (d, 2H, J=4.5 Hz), 7.39 (d, 1H, J=4.0 Hz), 7.48-7.54 (m, 2H), 7.79 (t, 1H, J=4.5 Hz), 7.82-7.86 (m, 1H), 7.95 (dd, 1H, J=1.0, 7.5 Hz). APCI/ESI MS m/z 480.1 [M+H]+

REFERENCES

1. Pizzolato, J. F. & Saltz, L. B. The camptothecins. *Lancet* 361, 2235-42 (2003).
2. Smith, N. F., Figg, W. D. & Sparreboom, A. Pharmacogenetics of irinotecan metabolism and transport: an update. *Toxicol In Vitro* 20, 163-75 (2006).
3. Pommier, Y. Topoisomerase I inhibitors: camptothecins and beyond. *Nat Rev Cancer* 6, 789-802 (2006).
4. Hsiang, Y. H., Hertzberg, R., Hecht, S. & Liu, L. F. Camptothecin induces protein-linked DNA breaks via mammalian DNA topoisomerase I. *J Biol Chem* 260, 14873-8 (1985).
5. Redinbo, M. R., Champoux, J. J. & Hol, W. G. Structural insights into the function of type IB topoisomerases. *Curr Opin Struct Biol* 9, 29-36 (1999).
6. Redinbo, M. R., Stewart, L., Kuhn, P., Champoux, J. J. & Hol, W. G. Crystal structures of human topoisomerase I in covalent and noncovalent complexes with DNA. *Science* 279, 1504-13 (1998).
7. Stewart, L., Redinbo, M. R., Qiu, X., Hol, W. G. & Champoux, J. J. A model for the mechanism of human topoisomerase I. *Science* 279, 1534-41 (1998).
8. Chrencik, J. E. et al. Mechanisms of camptothecin resistance by human topoisomerase I mutations. *J Mol Biol* 339, 773-84 (2004).
9. Staker, B. L. et al. The mechanism of topoisomerase I poisoning by a camptothecin analog. *Proc Natl Acad Sci USA* 99, 15387-92 (2002).
10. Mathijssen, R. H. J. et al. Clinical Pharmacokinetics and Metabolism of Irinotecan (CPT-11). *Clin Cancer Res* 7, 2182-2194 (2001).
11. Ma, M. K. & McLeod, H. L. Lessons learned from the irinotecan metabolic pathway. *Curr Med Chem* 10, 41-9 (2003).
12. Nagar, S. & Blanchard, R. L. Pharmacogenetics of uridine diphosphoglucuronosyltransferase (UGT) 1A family members and its role in patient response to irinotecan. *Drug Metab Rev* 38, 393-409 (2006).
13. Tobin, P. J., Dodds, H. M., Clarke, S., Schnitzler, M. & Rivory, L. P. The relative contributions of carboxylesterase and beta-glucuronidase in the formation of SN-38 in human colorectal tumours. *Oncol Rep* 10, 1977-9 (2003).
14. Fittkau, M., Voigt, W., Holzhausen, H. J. & Schmoll, H. J. Saccharic acid 1.4-lactone protects against CPT-11-induced mucosa damage in rats. *J Cancer Res Clin Oncol* 130, 388-94 (2004).
15. Flieger, D. et al. Phase II clinical trial for prevention of delayed diarrhea with cholestyramine/levofloxacin in the second-line treatment with irinotecan biweekly in patients with metastatic colorectal carcinoma. *Oncology* 72, 10-6 (2007).
16. Cummings, J. H. & Macfarlane, G. T. Role of intestinal bacteria in nutrient metabolism. *JPEN J Parenter Enteral Nutr* 21, 357-65 (1997).
17. Guarner, F. & Malagelada, J. R. Gut flora in health and disease. *Lancet* 361, 512-519 (2003).
18. Job, M. L. & Jacobs, N. F., Jr. Drug-induced *Clostridium difficile*-associated disease. *Drug Saf* 17, 37-46 (1997).
19. Levy, S. B. & Marshall, B. Antibacterial resistance worldwide: causes, challenges and responses. *Nat Med* 10, S 122-9 (2004).
20. Nord, C. E., Kager, L. & Heimdahl, A. Impact of antimicrobial agents on the gastrointestinal microflora and the risk of infections. *Am J Med* 76, 99-106 (1984).
21. Settle, C. D. & Wilcox, M. H. Review article: antibiotic-induced *Clostridium difficile* infection. *Aliment Pharmacol Ther* 10, 835-41 (1996).
22. Sears, S., McNally, P., Bachinski, M. S. & Avery, R. Irinotecan (CPT-11) induced colitis: report of a case and review of Food and Drug Administration MEDWATCH reporting. *Gastrointest Endosc* 50, 841-4 (1999).
23. Stamp, D. Antibiotic therapy may induce cancers in the colon and breasts through a mechanism involving bile acids and colonic bacteria. *Med Hypotheses* 63, 555-6 (2004).
24. Yang, L. & Pei, Z. Bacteria, inflammation, and colon cancer. *World J Gastroenterol* 12, 6741-6 (2006).
25. Basinska, A. & Florianczyk, B. Beta-glucuronidase in physiology and disease. *Ann Univ Mariae Curie Sklodowska Med* 58, 386-9 (2003).
26. Farnleitner, A. H., Hocke, L., Beiwl, C., Kavka, G. C. & Mach, R. L. Hydrolysis of 4-methylumbelliferyl-beta-D-glucuronide in differing sample fractions of river waters and its implication for the detection of fecal pollution. *Water Res.* 36, 975-981 (2002).
27. Russell, W. M. & Klaenhammer, T. R. Identification and cloning of gusA, encoding a new beta-glucuronidase from *Lactobacillus gasseri* ADH. *Appl Environ Microbiol* 67, 1253-61 (2001).

TABLE 1

| Compound ID | Structure | IC50 (μm) |
|---|---|---|
| BRITE-354972 | 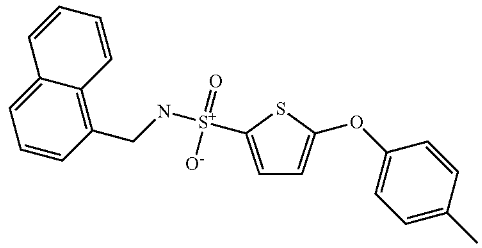 [SMILES: Cc1ccc(Oc2ccc([S+](=O)([O-])NCc3cccc4ccccc34)s2)cc1] | 0.000 |
| BRITE-355123 | 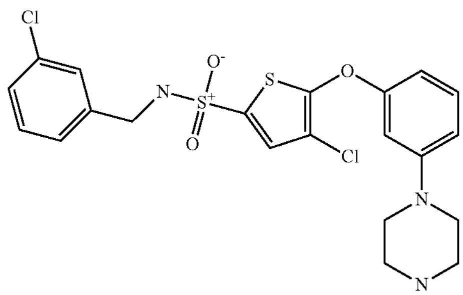 [SMILES: O=[S+]([O-])(NCc1cccc(Cl)c1)c1cc(Cl)c(Oc2cccc(N3CCNCC3)c2)s1] | 0.090 |
| BRITE-355252 | 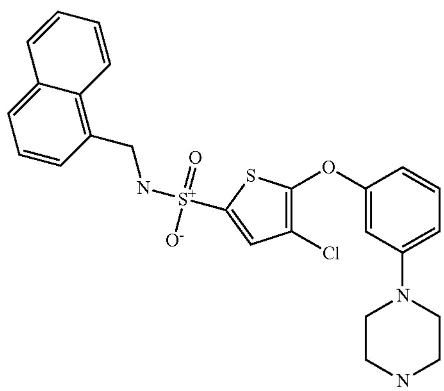 [SMILES: O=[S+]([O-])(NCc1cccc2ccccc12)c1cc(Cl)c(Oc2cccc(N3CCNCC3)c2)s1] | 0.090 |
| BRITE-354975 | 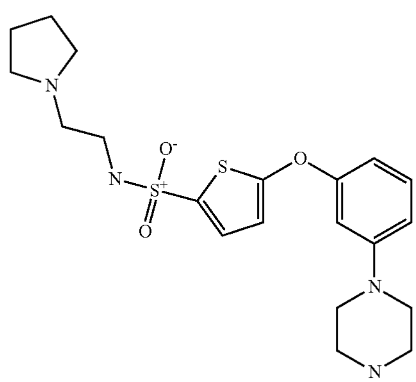 [SMILES: O=[S+]([O-])(NCCN1CCCC1)c1ccc(Oc2cccc(N3CCNCC3)c2)s1] | 0.120 |
| BRITE-354989 | 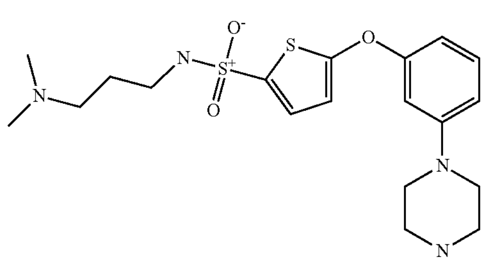 [SMILES: CN(C)CCCN[S+](=O)([O-])c1ccc(Oc2cccc(N3CCNCC3)c2)s1] | 0.150 |

TABLE 1-continued

β-Glucuronidase Inhibitory activity of phenoxythiophene sulfonamides

| Compound ID | Structure | IC50 (μm) |
|---|---|---|
| BRITE-354909 | 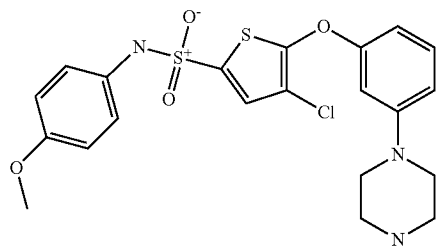 [SMILES: COc1ccc(N[S+](=O)([O-])c2cc(Cl)c(Oc3cccc(N4CCNCC4)c3)s2)cc1] | 0.170 |
| BRITE-354725 | 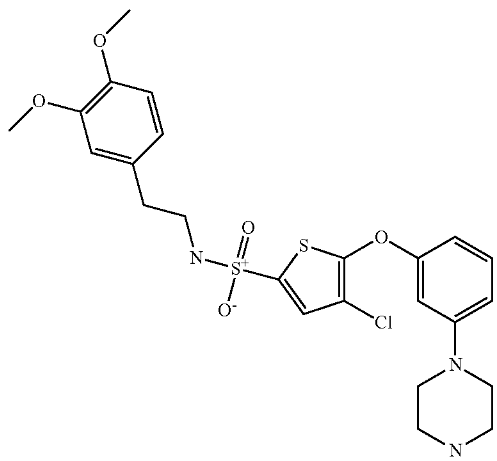 [SMILES: COc1ccc(CCN[S+](=O)([O-])c2cc(Cl)c(Oc3cccc(N4CCNCC4)c3)s2)cc1OC] | 0.190 |
| BRITE-354969 | 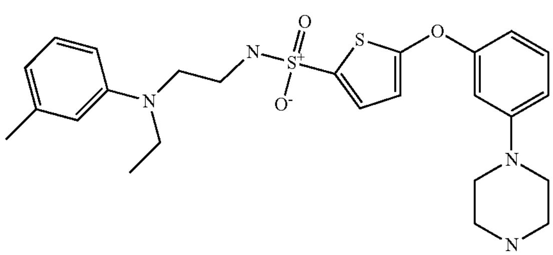 [SMILES: CCN(CCN[S+](=O)([O-])c1ccc(Oc2cccc(N3CCNCC3)c2)s1)c1cccc(C)c1] | 0.200 |
| BRITE-355417 | 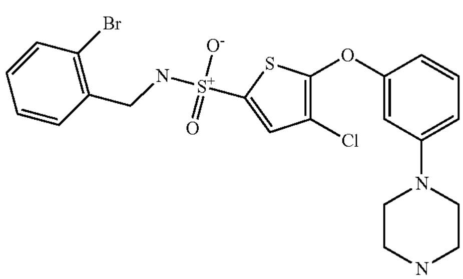 [SMILES: O=[S+]([O-])(NCc1ccccc1Br)c1cc(Cl)c(Oc2cccc(N3CCNCC3)c2)s1] | 0.210 |
| BRITE-355006 | 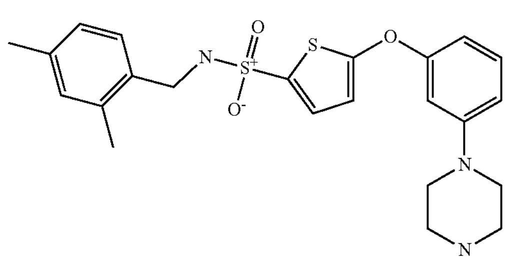 [SMILES: Cc1ccc(CN[S+](=O)([O-])c2ccc(Oc3cccc(N4CCNCC4)c3)s2)c(C)c1] | 0.210 |

TABLE 1-continued

β-Glucuronidase Inhibitory activity of phenoxythiophene sulfonamides

| Compound ID | Structure | IC50 (μm) |
| --- | --- | --- |
| BRITE-355017 | 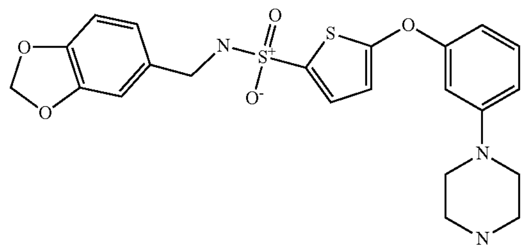 [SMILES: O=[S+]([O-])(NCc1ccc2c(c1)OCO2)c1ccc(Oc2cccc(N3CCNCC3)c2)s1] | 0.220 |
| BRITE-354979 | 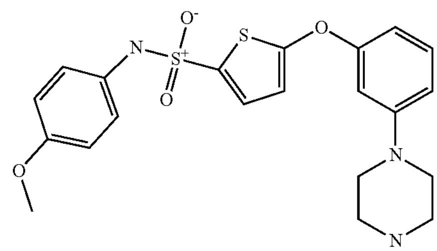 [SMILES: COc1ccc(N[S+](=O)([O-])c2ccc(Oc3cccc(N4CCNCC4)c3)s2)cc1] | 0.230 |
| BRITE-355004 | 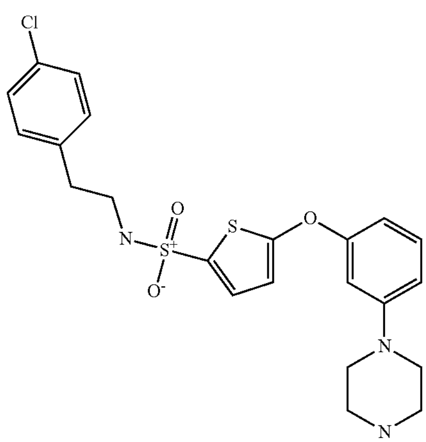 [SMILES: O=[S+]([O-])(NCCc1ccc(Cl)cc1)c1ccc(Oc2cccc(N3CCNCC3)c2)s1] | 0.240 |
| BRITE-354667 | 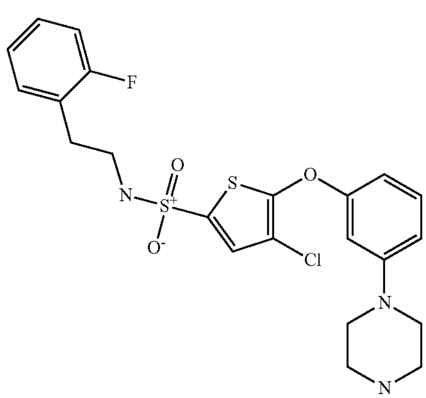 [SMILES: O=[S+]([O-])(NCCc1ccccc1F)c1cc(Cl)c(Oc2cccc(N3CCNCC3)c2)s1] | 0.270 |

TABLE 1-continued

β-Glucuronidase Inhibitory activity of phenoxythiophene sulfonamides

| Compound ID | Structure | IC50 (μm) |
|---|---|---|
| BRITE-354966 | 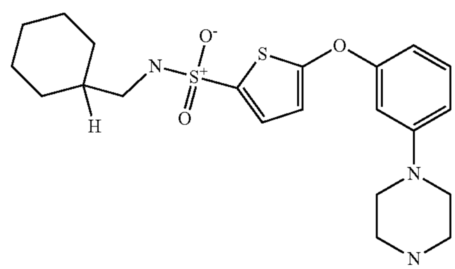 [SMILES: O=[S+]([O-])(NCC1CCCCC1)c1ccc(Oc2cccc(N3CCNCC3)c2)s1] | 0.270 |
| BRITE-355262 | 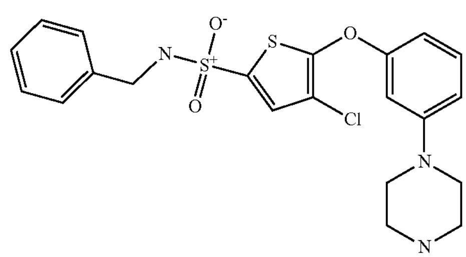 [SMILES: O=[S+]([O-])(NCc1ccccc1)c1cc(Cl)c(Oc2cccc(N3CCNCC3)c2)s1] | 0.280 |
| BRITE-354965 | 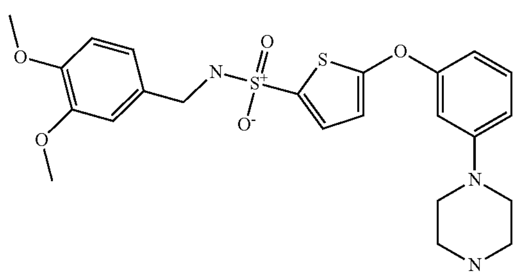 [SMILES: COc1ccc(CN[S+](=O)([O-])c2ccc(Oc3cccc(N4CCNCC4)c3)s2)cc1OC] | 0.290 |
| BRITE-354873 | 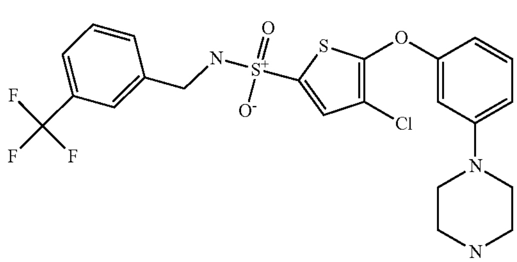 [SMILES: O=[S+]([O-])(NCc1cccc(C(F)(F)F)c1)c1cc(Cl)c(Oc2cccc(N3CCNCC3)c2)s1] | 0.290 |
| BRITE-354615 | 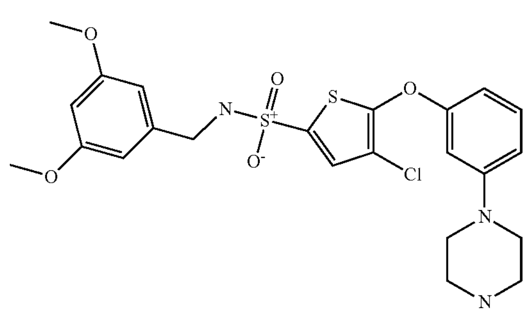 [SMILES: COc1cc(CN[S+](=O)([O-])c2cc(Cl)c(Oc3cccc(N4CCNCC4)c3)s2)cc(OC)c1] | 0.310 |

TABLE 1-continued

β-Glucuronidase Inhibitory activity of phenoxythiophene sulfonamides

| Compound ID | Structure | IC50 (μm) |
| --- | --- | --- |
| BRITE-355016 | 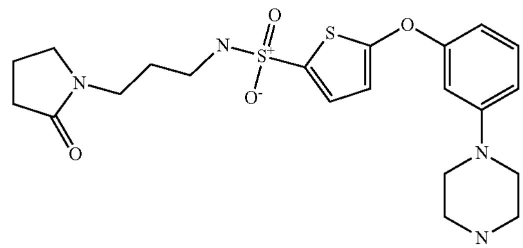 [SMILES: O=C1CCCN1CCCN[S+](=O)([O-])c1ccc(Oc2cccc(N3CCNCC3)c2)s1] | 0.320 |
| BRITE-354517 | 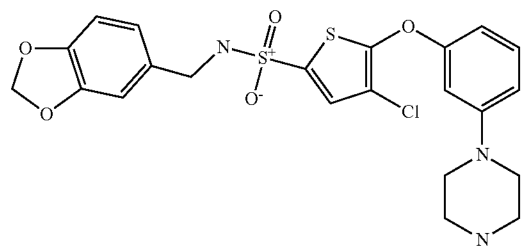 [SMILES: O=[S+]([O-])(NCc1ccc2c(c1)OCO2)c1cc(Cl)c(Oc2cccc(N3CCNCC3)c2)s1] | 0.320 |
| BRITE-354958 | 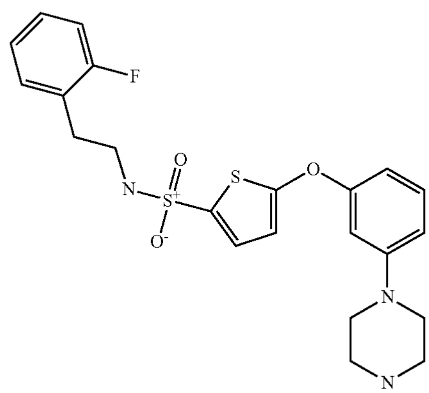 [SMILES: O=[S+]([O-])(NCCc1ccccc1F)c1ccc(Oc2cccc(N3CCNCC3)c2)s1] | 0.330 |
| BRITE-355360 | 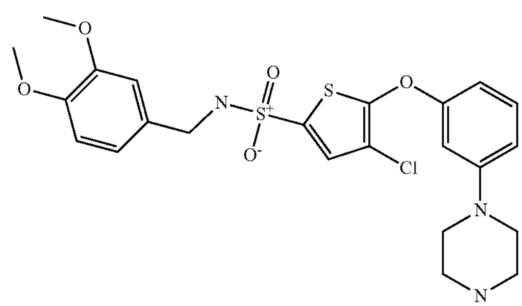 [SMILES: COc1ccc(CN[S+](=O)([O-])c2cc(Cl)c(Oc3cccc(N4CCNCC4)c3)s2)cc1OC] | 0.340 |
| BRITE-355227 | 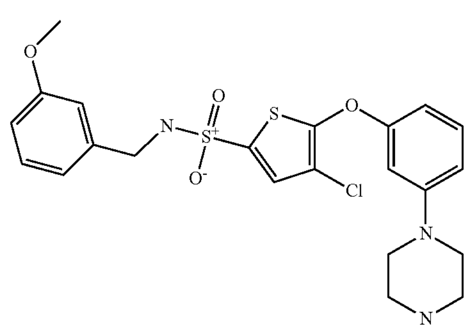 [SMILES: COc1cccc(CN[S+](=O)([O-])c2cc(Cl)c(Oc3cccc(N4CCNCC4)c3)s2)c1] | 0.350 |

TABLE 1-continued
β-Glucuronidase Inhibitory activity of phenoxythiophene sulfonamides
| Compound ID | Structure | IC50 (μm) |
|---|---|---|
| BRITE-354948 | 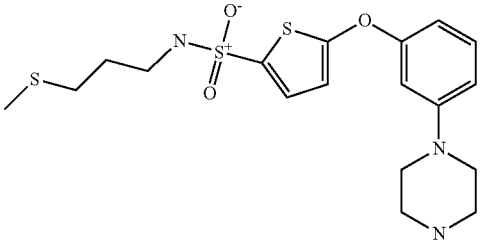 [SMILES: CSCCCN[S+](=O)([O-])c1ccc(Oc2cccc(N3CCNCC3)c2)s1] | 0.390 |
| BRITE-355336 | 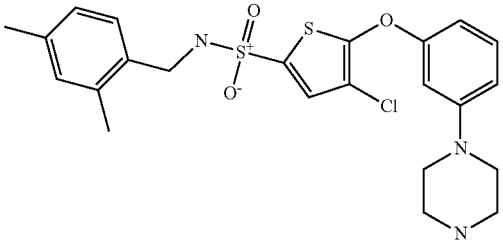 [SMILES: Cc1ccc(CN[S+](=O)([O-])c2cc(Cl)c(Oc3cccc(N4CCNCC4)c3)s2)c(C)c1] | 0.410 |
| BRITE-355423 | 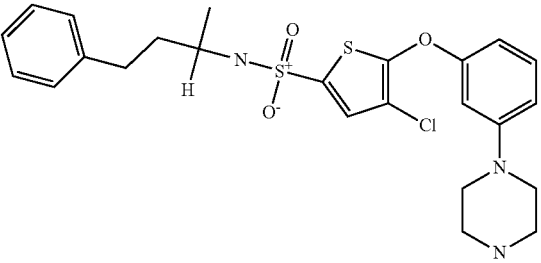 [SMILES: CC(CCc1ccccc1)N[S+](=O)([O-])c1cc(Cl)c(Oc2cccc(N3CCNCC3)c2)s1] | 0.430 |
| BRITE-355468 | 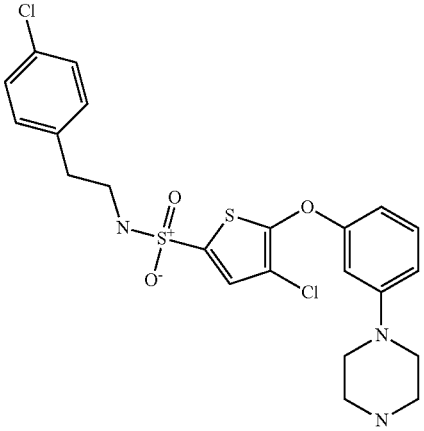 [SMILES: O=[S+]([O-])(NCCc1ccc(Cl)cc1)c1cc(Cl)c(Oc2cccc(N3CCNCC3)c2)s1] | 0.500 |
| BRITE-355202 | 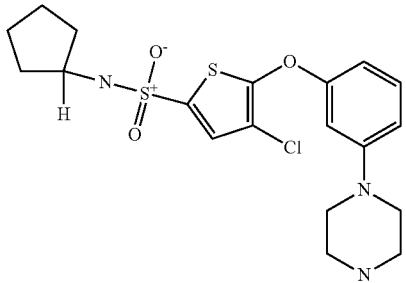 [SMILES: O=[S+]([O-])(NC1CCCC1)c1cc(Cl)c(Oc2cccc(N3CCNCC3)c2)s1] | 0.510 |

TABLE 1-continued
β-Glucuronidase Inhibitory activity of phenoxythiophene sulfonamides
| Compound ID | Structure | IC50 (μm) |
|---|---|---|
| BRITE-355003 | 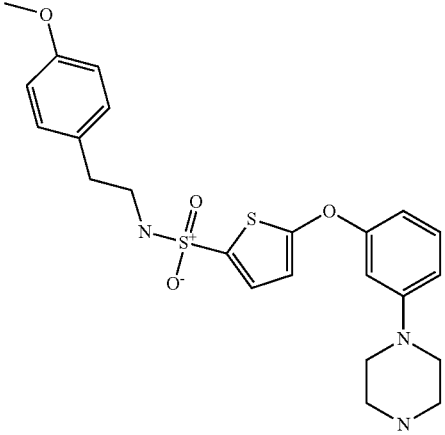 [SMILES: COc1ccc(CCN[S+](=O)([O-])c2ccc(Oc3cccc(N4CCNCC4)c3)s2)cc1] | 0.510 |
| BRITE-354946 | 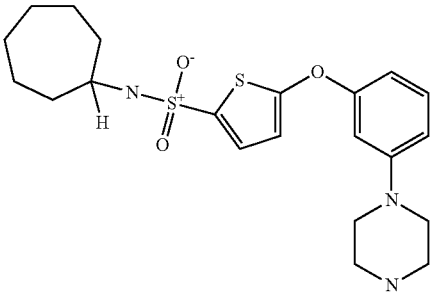 [SMILES: O=[S+]([O-])(NC1CCCCCC1)c1ccc(Oc2cccc(N3CCNCC3)c2)s1] | 0.560 |
| BRITE-354983 | 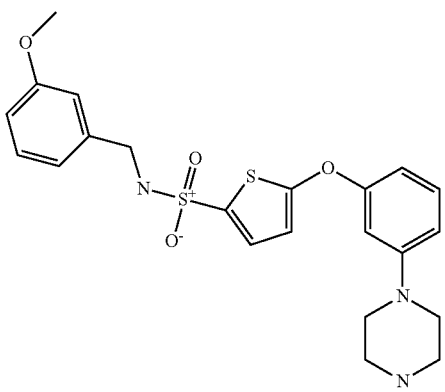 [SMILES: COc1cccc(CN[S+](=O)([O-])c2ccc(Oc3cccc(N4CCNCC4)c3)s2)c1] | 0.570 |
| BRITE-355014 | 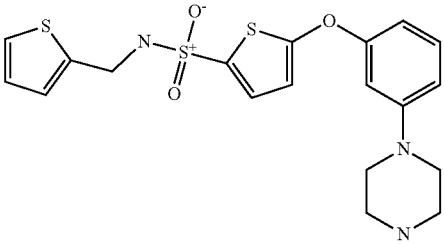 [SMILES: O=[S+]([O-])(NCc1cccs1)c1ccc(Oc2cccc(N3CCNCC3)c2)s1] | 0.600 |

TABLE 1-continued
| β-Glucuronidase Inhibitory activity of phenoxythiophene sulfonamides | | |
|---|---|---|
| Compound ID | Structure | IC50 (μm) |
| BRITE-355015 | 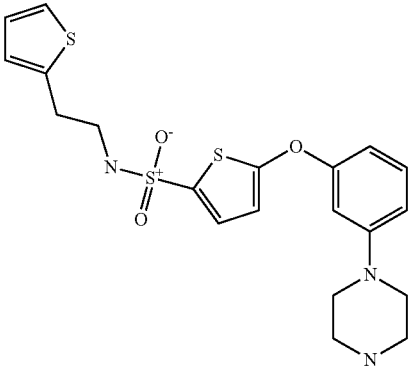 [SMILES: O=[S+]([O-])(NCCc1cccs1)c1ccc(Oc2cccc(N3CCNCC3)c2)s1] | 0.630 |
| BRITE-354627 | 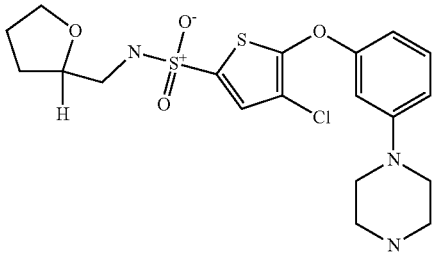 [SMILES: O=[S+]([O-])(NCC1CCCO1)c1cc(Cl)c(Oc2cccc(N3CCNCC3)c2)s1] | 0.710 |
| BRITE-354764 | 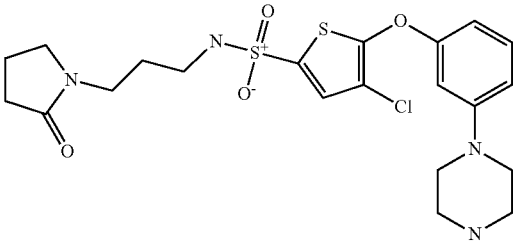 [SMILES: O=C1CCCN1CCCN[S+](=O)([O-])c1cc(Cl)c(Oc2cccc(N3CCNCC3)c2)s1] | 0.730 |
| BRITE-354993 | 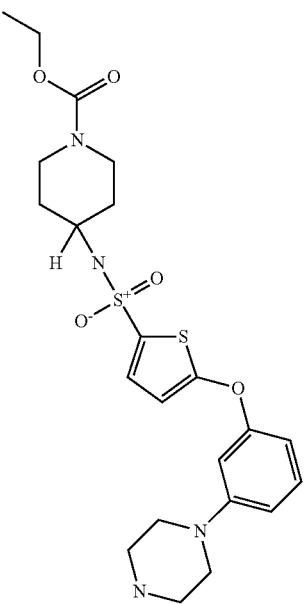 [SMILES: CCOC(=O)N1CCC(N[S+](=O)([O-])c2ccc(Oc3cccc(N4CCNCC4)c3)s2)CC1] | 0.730 |

TABLE 1-continued

β-Glucuronidase Inhibitory activity of phenoxythiophene sulfonamides

| Compound ID | Structure | IC50 (μm) |
|---|---|---|
| BRITE-354956 | 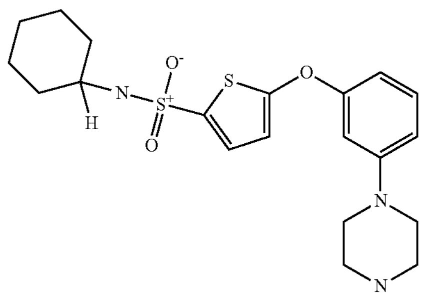 [SMILES: O=[S+]([O-])(NC1CCCCC1)c1ccc(Oc2cccc(N3CCNCC3)c2)s1] | 0.750 |
| BRITE-354984 | 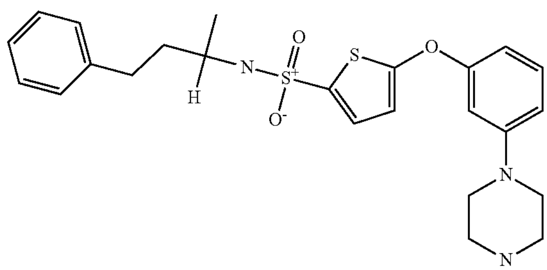 [SMILES: CC(CCc1ccccc1)N[S+](=O)([O-])c1ccc(Oc2cccc(N3CCNCC3)c2)s1] | 0.750 |
| BRITE-354974 | 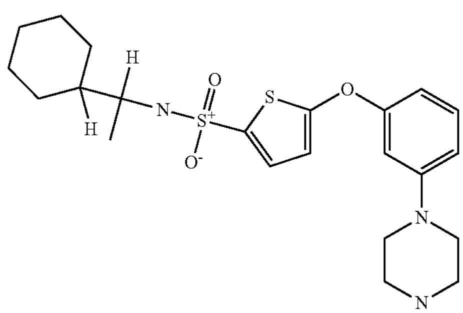 [SMILES: CC(N[S+](=O)([O-])c1ccc(Oc2cccc(N3CCNCC3)c2)s1)C1CCCCC1] | 0.760 |
| BRITE-354947 | 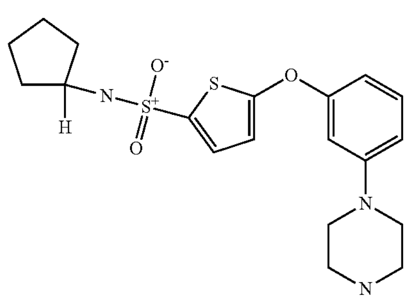 [SMILES: O=[S+]([O-])(NC1CCCC1)c1ccc(Oc2cccc(N3CCNCC3)c2)s1] | 0.770 |

TABLE 1-continued
β-Glucuronidase Inhibitory activity of phenoxythiophene sulfonamides
| Compound ID | Structure | IC50 (μm) |
|---|---|---|
| BRITE-354392 | 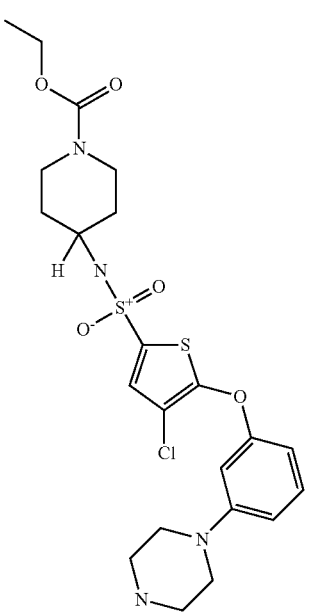 [SMILES: CCOC(=O)N1CCC(N[S+](=O)([O-])c2cc(Cl)c(Oc3cccc(N4CCNCC4)c3)s2)CC1] | 0.790 |
| BRITE-355045 | 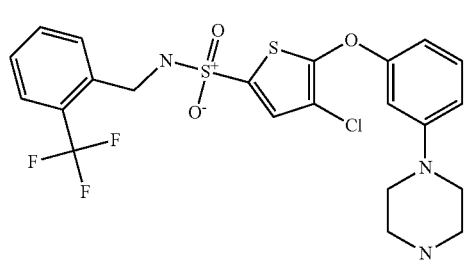 [SMILES: O=[S+]([O-])(NCc1ccccc1C(F)(F)F)c1cc(Cl)c(Oc2cccc(N3CCNCC3)c2)s1] | 0.880 |
| BRITE-354994 | 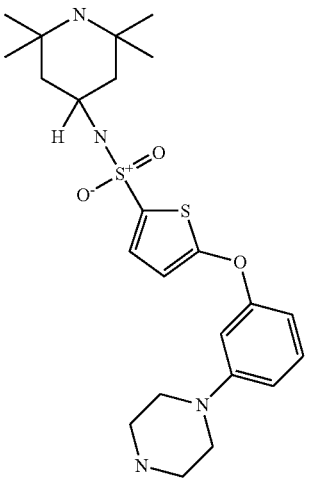 [SMILES: CC1(C)CC(N[S+](=O)([O-])c2ccc(Oc3cccc(N4CCNCC4)c3)s2)CC(C)(C)N1] | 0.900 |

TABLE 1-continued

| β-Glucuronidase Inhibitory activity of phenoxythiophene sulfonamides | | |
|---|---|---|
| Compound ID | Structure | IC50 (μm) |
| BRITE-354957 | | 0.920 |
| BRITE-355074 | | 0.970 |
| BRITE-354565 | | 1.000 |
| BRITE-354998 | | 1.000 |
| BRITE-354955 | | 1.310 |

TABLE 1-continued

β-Glucuronidase Inhibitory activity of phenoxythiophene sulfonamides

| Compound ID | Structure | IC50 (μm) |
|---|---|---|
| BRITE-355296 | 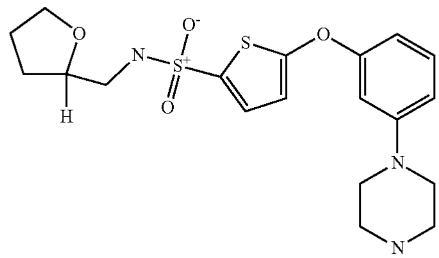 [SMILES: O=[S+]([O-])(NCC1CCCO1)c1ccc(Oc2cccc(N3CCNCC3)c2)s1] | 1.370 |
| BRITE-355008 | 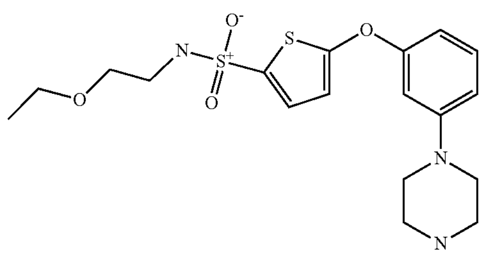 | 1.390 |
| BRITE-355005 | 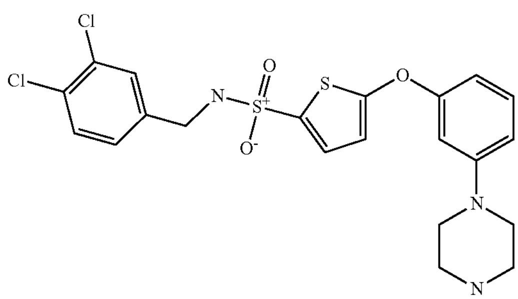 [SMILES: O=[S+]([O-])(NCc1ccc(Cl)c(Cl)c1)c1ccc(Oc2cccc(N3CCNCC3)c2)s1] | 6.700 |
| BRITE-355192 | 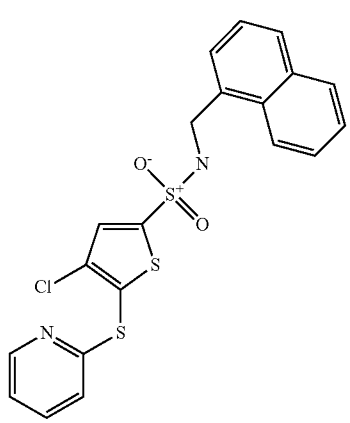 [SMILES: O=[S+]([O-])(NCc1cccc2ccccc12)c1cc(Cl)c(Sc2ccccn2)s1] | 16.140 |

TABLE 1-continued

β-Glucuronidase Inhibitory activity of phenoxythiophene sulfonamides

| Compound ID | Structure | IC50 (μm) |
| --- | --- | --- |
| BRITE-354839 | 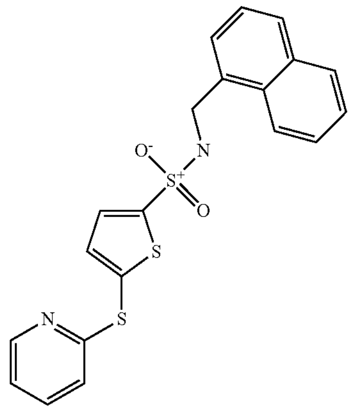 [SMILES: O=[S+]([O-])(NCc1cccc2ccccc12)c1ccc(Sc2ccccn2)s1] | 20.030 |
| BRITE-354428 | 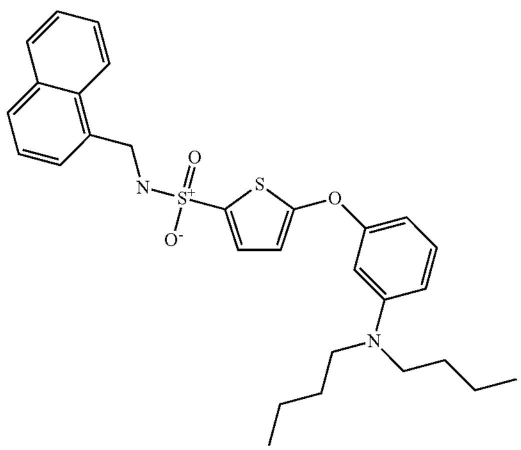 [SMILES: CCCCN(CCCC)c1cccc(Oc2ccc([S+](=O)([O-])NCc3cccc4ccccc34)s2)c1] | 20.560 |
| BRITE-355224 | 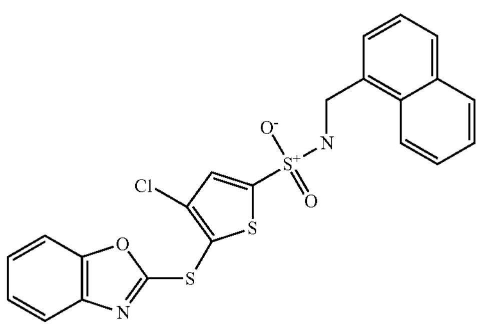 [SMILES: O=[S+]([O-])(NCc1cccc2ccccc12)c1cc(Cl)c(Sc2nc3ccccc3o2)s1] | 22.910 |
| BRITE-355018 | 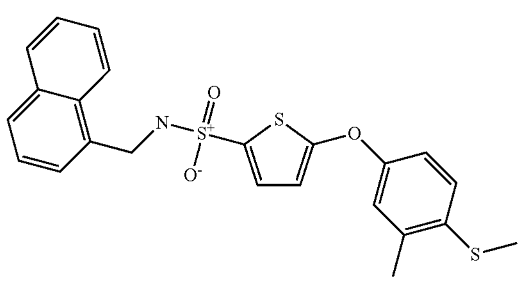 [SMILES: CSc1ccc(Oc2ccc([S+](=O)([O-])NCc3cccc4ccccc34)s2)cc1C] | 23.330 |

TABLE 1-continued

| β-Glucuronidase Inhibitory activity of phenoxythiophene sulfonamides | | |
|---|---|---|
| Compound ID | Structure | IC50 (μm) |
| BRITE-355240 | | 28.570 |
| BRITE-355329 | | 31.510 |
| BRITE-355250 | | 50.060 |
| BRITE-355339 | | 76.560 |

TABLE 1-continued

β-Glucuronidase Inhibitory activity of phenoxythiophene sulfonamides

| Compound ID | Structure | IC50 (μm) |
|---|---|---|
| BRITE-355319 | 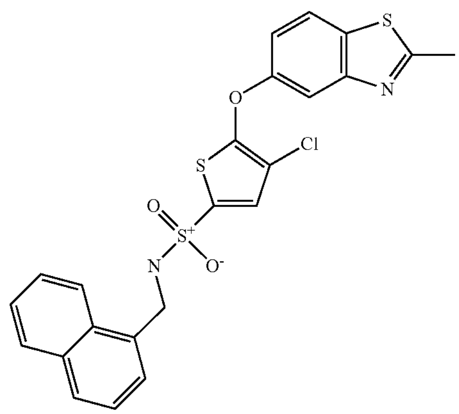 [SMILES: Cc1nc2cc(Oc3sc([S+](=O)([O-])NCc4cccc5ccccc45)cc3Cl)ccc2s1] | 84.560 |
| BRITE-355243 | 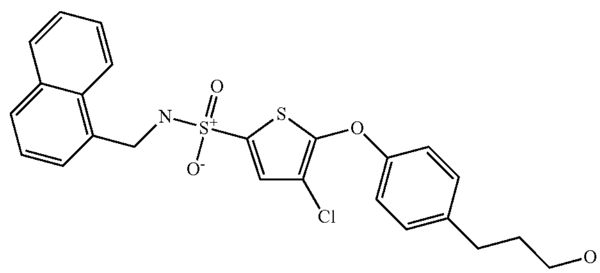 [SMILES: O=[S+]([O-])(NCc1cccc2ccccc12)c1cc(Cl)c(Oc2ccc(CCCO)cc2)s1] | 92.780 |
| BRITE-355180 | 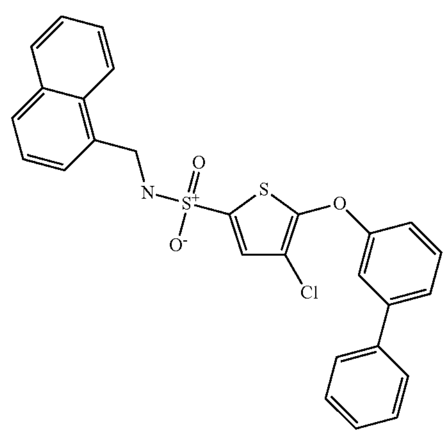 [SMILES: O=[S+]([O-])(NCc1cccc2ccccc12)c1cc(Cl)c(Oc2cccc(-c3ccccc3)c2)s1] | 101.980 |
| BRITE-355244 | 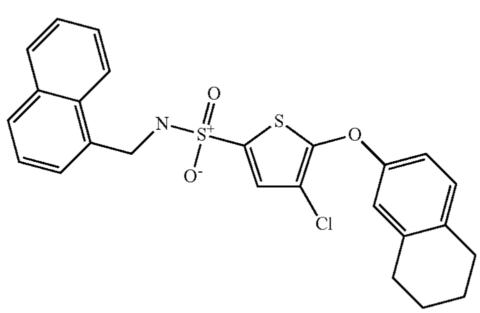 [SMILES: O=[S+]([O-])(NCc1cccc2ccccc12)c1cc(Cl)c(Oc2ccc3c(c2)CCCC3)s1] | 123.470 |

TABLE 1-continued

β-Glucuronidase Inhibitory activity of phenoxythiophene sulfonamides

| Compound ID | Structure | IC50 (μm) |
|---|---|---|
| BRITE-355214 | 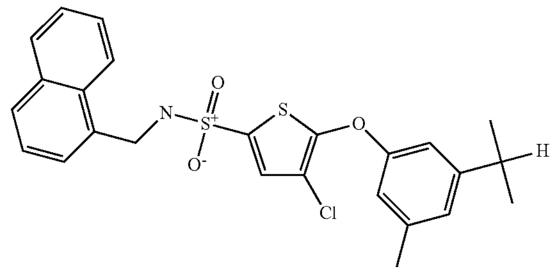 [SMILES: Cc1cc(Oc2sc([S+](=O)([O-])NCc3cccc4ccccc34)cc2Cl)cc(C(C)C)c1] | 134.850 |
| BRITE-355030 | 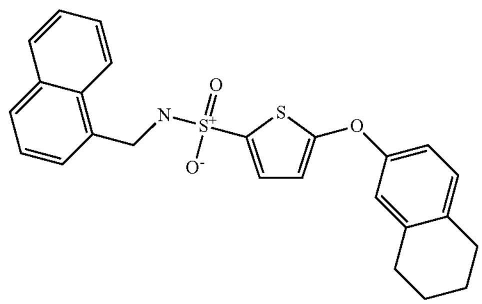 [SMILES: O=[S+]([O-])(NCc1cccc2ccccc12)c1ccc(Oc2ccc3c(c2)CCCC3)s1] | 149.400 |
| BRITE-355234 | 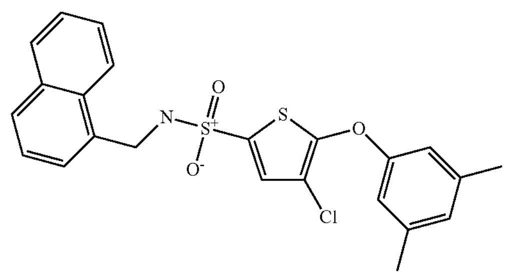 [SMILES: Cc1cc(C)cc(Oc2sc([S+](=O)([O-])NCc3cccc4ccccc34)cc2Cl)c1] | 151.550 |
| BRITE-355169 | 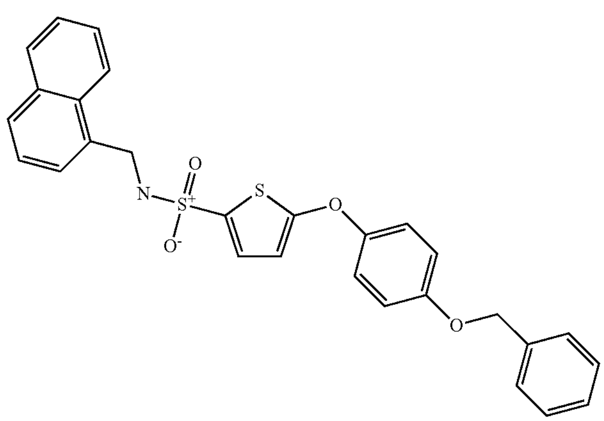 [SMILES: O=[S+]([O-])(NCc1cccc2ccccc12)c1ccc(Oc2ccc(OCc3ccccc3)cc2)s1] | 152.600 |

TABLE 1-continued

β-Glucuronidase Inhibitory activity of phenoxythiophene sulfonamides

| Compound ID | Structure | IC50 (μm) |
|---|---|---|
| BRITE-354458 | 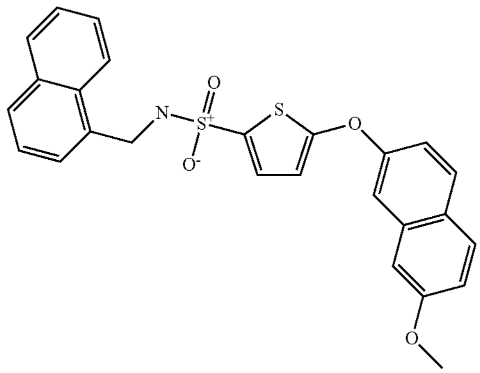 [SMILES: COc1ccc2ccc(Oc3ccc([S+](=O)([O-])NCc4cccc5ccccc45)s3)cc2c1] | 175.430 |
| BRITE-355211 | 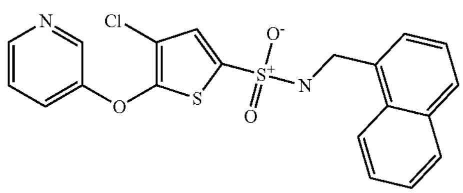 [SMILES: O=[S+]([O-])(NCc1cccc2ccccc12)c1cc(Cl)c(Oc2cccnc2)s1] | 192.490 |
| BRITE-355201 | 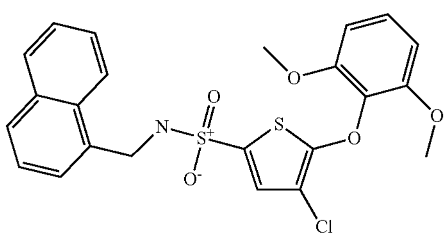 [SMILES: COc1cccc(OC)c1Oc1sc([S+](=O)([O-])NCc2cccc3ccccc23)cc1Cl] | 201.630 |
| BRITE-355233 | 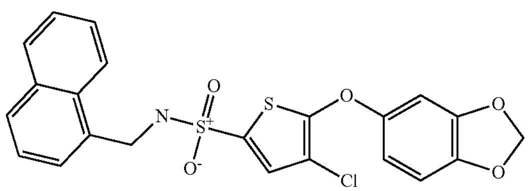 [SMILES: O=[S+]([O-])(NCc1cccc2ccccc12)c1cc(Cl)c(Oc2ccc3c(c2)OCO3)s1] | 375.580 |
| BRITE-355221 | 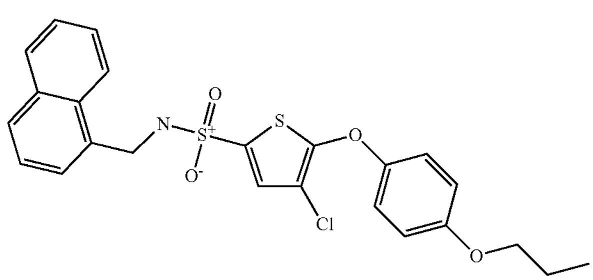 [SMILES: CCCOc1ccc(Oc2sc([S+](=O)([O-])NCc3cccc4ccccc34)cc2Cl)cc1] | 401.950 |
| BRITE-355253 | 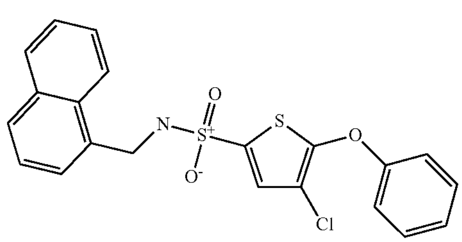 [SMILES: O=[S+]([O-])(NCc1cccc2ccccc12)c1cc(Cl)c(Oc2ccccc2)s1] | 443.900 |

TABLE 1-continued

β-Glucuronidase Inhibitory activity of phenoxythiophene sulfonamides

| Compound ID | Structure | IC50 (μm) |
|---|---|---|
| BRITE-354502 | 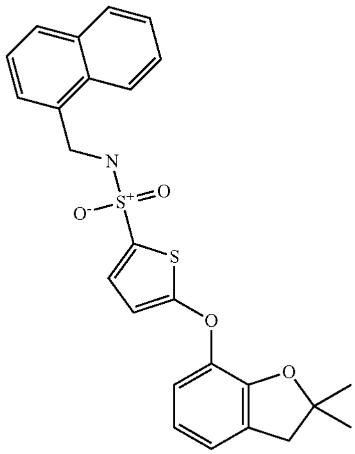 [SMILES: CC1(C)Cc2cccc(Oc3ccc([S+](=O)([O-])NCc4cccc5ccccc45)s3)c2O1] | 965.440 |

TABLE 2

Structure and β-Glucuronidase InhibitoryActivity of BRITE-355252 analogs

| Compound ID | Structure | IC50 (μM) |
|---|---|---|
| BRITE-354873 | 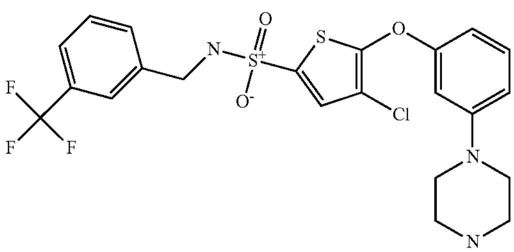 [SMILES: O=[S+]([O-])(NCc1cccc(C(F)(F)F)c1)c1cc(Cl)c(Oc2cccc(N3CCNCC3)c2)s1] | 0.030 |
| BRITE-354909 | 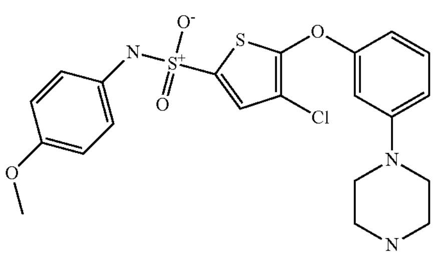 [SMILES: COc1ccc(N[S+](=O)([O-])c2cc(Cl)c(Oc3cccc(N4CCNCC4)c3)s2)cc1] | 0.060 |
| BRITE-355123 | 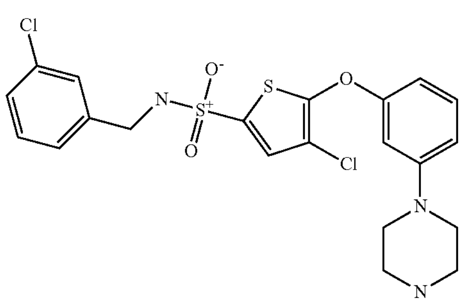 [SMILES: O=[S+]([O-])(NCc1cccc(Cl)c1)c1cc(Cl)c(Oc2cccc(N3CCNCC3)c2)s1] | 0.020 |

TABLE 2-continued

Structure and β-Glucuronidase InhibitoryActivity of BRITE-355252 analogs

| Compound ID | Structure | IC50 (µM) |
| --- | --- | --- |
| BRITE-355227 | 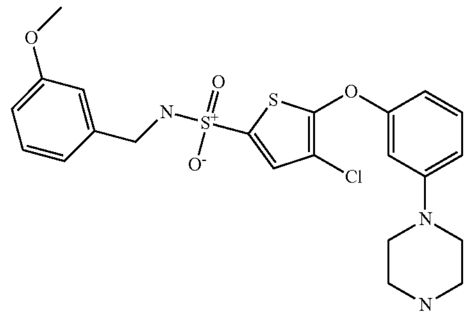 [SMILES: COc1cccc(CN[S+](=O)([O-])c2cc(Cl)c(Oc3cccc(N4CCNCC4)c3)s2)c1] | 0.050 |
| BRITE-355252 | 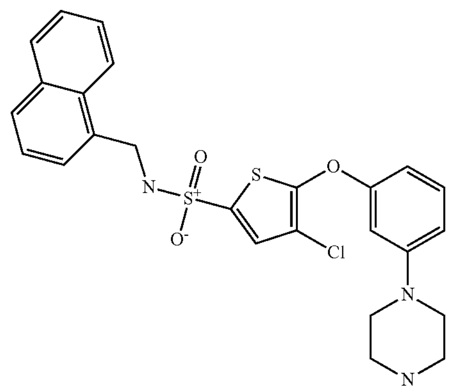 [SMILES: O=[S+]([O-])(NCc1cccc2ccccc12)c1cc(Cl)c(Oc2cccc(N3CCNCC3)c2)s1] | 0.020 |
| BRITE--492794 | 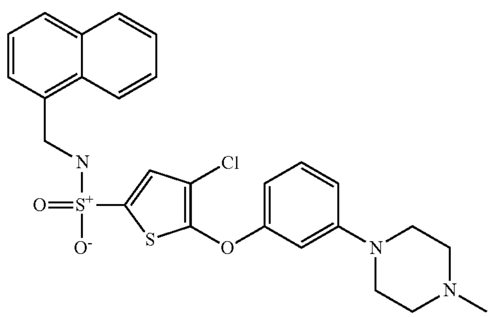 [SMILES: CN1CCN(c2cccc(Oc3sc([S+](=O)([O-])NCc4cccc5ccccc45)cc3Cl)c2)CC1] | 10.170 |
| BRITE--492796 | 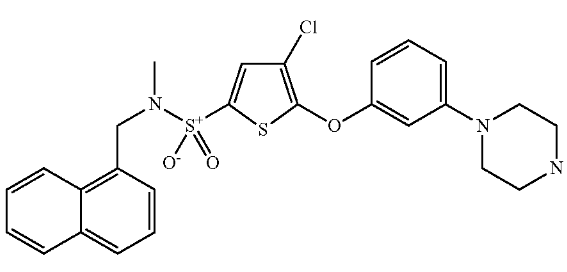 [SMILES: CN(Cc1cccc2ccccc12)[S+](=O)([O-])c1cc(Cl)c(Oc2cccc(N3CCNCC3)c2)s1] | 0.120 |
| BRITE--492797 | 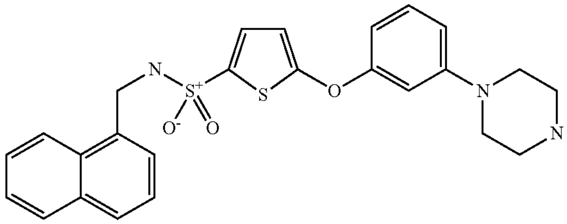 [SMILES: O=[S+]([O-])(NCc1cccc2ccccc12)c1ccc(Oc2cccc(N3CCNCC3)c2)s1] | 0.090 |

TABLE 2-continued

Structure and β-Glucuronidase InhibitoryActivity of BRITE-355252 analogs

| Compound ID | Structure | IC50 (μM) |
| --- | --- | --- |
| BRITE--492798 | 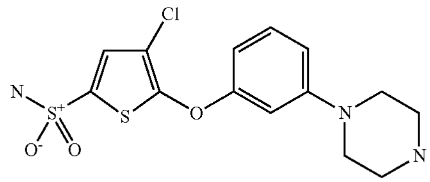 [SMILES: N[S+](=O)([O-])c1cc(Cl)c(Oc2cccc(N3CCNCC3)c2)s1] | 0.330 |
| BRITE--492799 | 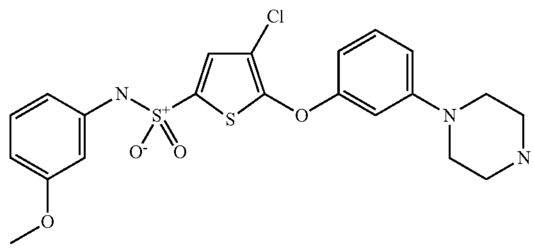 [SMILES: COc1cccc(N[S+](=O)([O-])c2cc(Cl)c(Oc3cccc(N4CCNCC4)c3)s2)c1] | 0.070 |
| BRITE--492800 | 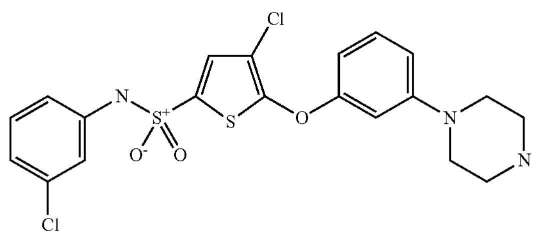 [SMILES: O=[S+]([O-])(Nc1cccc(Cl)c1)c1cc(Cl)c(Oc2cccc(N3CCNCC3)c2)s1] | 0.070 |
| BRITE--492802 | 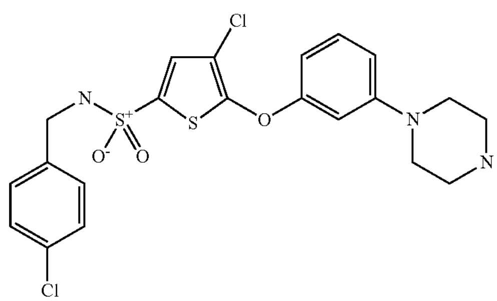 [SMILES: O=[S+]([O-])(NCc1ccc(Cl)cc1)c1cc(Cl)c(Oc2cccc(N3CCNCC3)c2)s1] | 0.030 |
| BRITE--492803 | 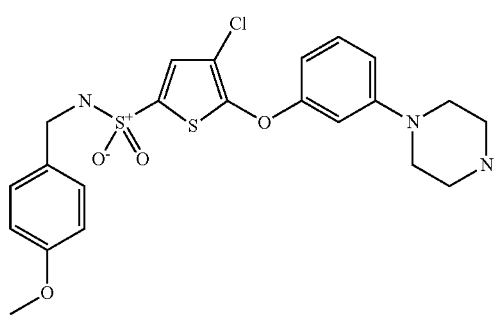 [SMILES: COc1ccc(CN[S+](=O)([O-])c2cc(Cl)c(Oc3cccc(N4CCNCC4)c3)s2)cc1] | 0.100 |
| BRITE--492805 | 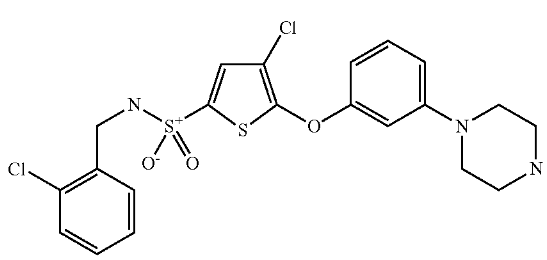 [SMILES: O=[S+]([O-])(NCc1ccccc1Cl)c1cc(Cl)c(Oc2cccc(N3CCNCC3)c2)s1] | 0.040 |

TABLE 2-continued

Structure and β-Glucuronidase Inhibitory Activity of BRITE-355252 analogs

| Compound ID | Structure | IC50 (µM) |
|---|---|---|
| BRITE--492806 | 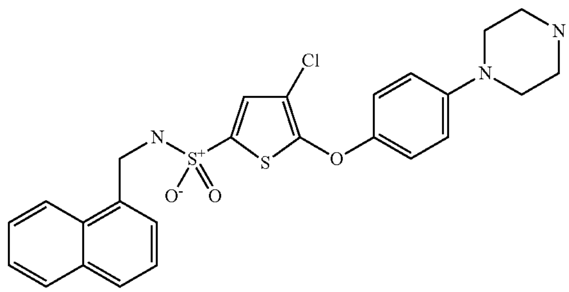 [SMILES: O=[S+]([O-])(NCc1cccc2ccccc12)c1cc(Cl)c(Oc2ccc(N3CCNCC3)cc2)s1] | 0.300 |
| BRITE--492807 | 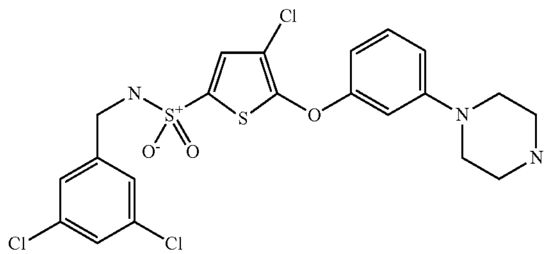 [SMILES: O=[S+]([O-])(NCc1cc(Cl)cc(Cl)c1)c1cc(Cl)c(Oc2cccc(N3CCNCC3)c2)s1] | 0.130 |
| BRITE--492808 | 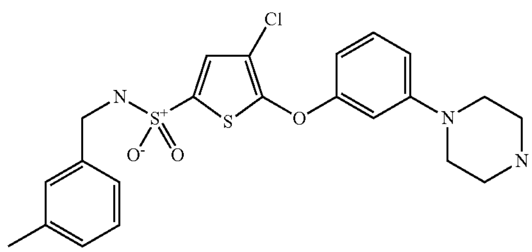 [SMILES: Cc1cccc(CN[S+](=O)([O-])c2cc(Cl)c(Oc3cccc(N4CCNCC4)c3)s2)c1] | 0.030 |
| BRITE--492809 | 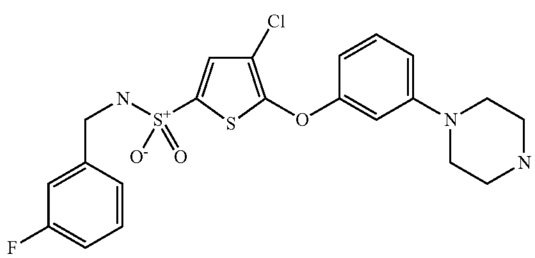 [SMILES: O=[S+]([O-])(NCc1cccc(F)c1)c1cc(Cl)c(Oc2cccc(N3CCNCC3)c2)s1] | 0.040 |

The invention claimed is:

1. A method of inhibiting glucuronidase comprising administering to a subject an amount of a compound or a pharmaceutically acceptable salt of the compound that is effective as an inhibitor of glucuronidase, wherein the compound is of formula

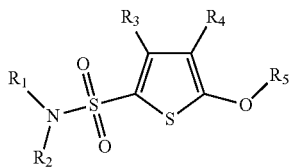

(I)

or a pharmaceutically acceptable salt thereof
wherein:
each of $R_1$ and $R_2$ is the same or different and is selected from H, naphthalene, naphthalene-($C_1$-$C_4$) alkyl, 3-(trifluoromethyl)benzyl, 3-(trichloromethyl)benzyl, 3-(tribromomethyl) benzyl, 3-(triiodomethyl)benzyl, 3-($C_1$-$C_4$ alkyl)-benzyl, 3,5-dichlorobenzyl, 3,5-difluorobenzyl, 3,5,-dibromobenzyl, 3,5-diiodobenzyl, 3-chlorophenyl, 3-fluorophenyl, 3-bromophenyl, 3-iodophenyl, 3-($C_1$-$C_4$ alkyoxy) phenyl, 4-($C_1$-$C_4$ alkyoxy) phenyl, 2-chlorobenzyl, 3-chlorobenzyl, 4-chlorobenzyl, 2-fluorobenzyl, 3-fluorobenzyl, 4-fluorobenzyl, 2-bromobenzyl, 3-bromobenzyl, 4-bromobenzyl, 2-iodobenzyl, 3-iodobenzyl, 4-iodobenzyl, 3-($C_1$-$C_4$ alkyoxy) benzyl; and 4-($C_1$-$C_4$ alkyoxy)benzyl;

each of $R_3$ and $R_4$ is the same or different and is selected from H, F, Cl, Br, and I, and $R_5$ is selected from 3-(R-1-yl)phenyl and 4-(R-1-yl)phenyl, wherein R is selected from piperazin, or 4-($C_1$-$C_4$ alkyl) piperazin.

2. The method of claim 1, wherein the compound is

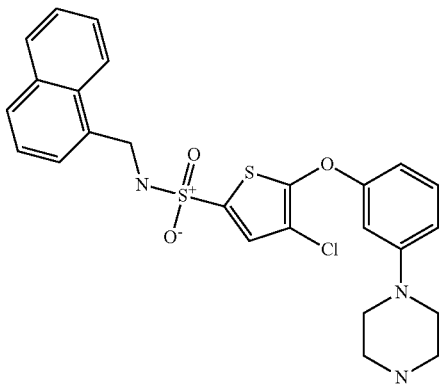 [SMILES: O=[S+]([O-])(NCc1cccc2ccccc12)c1cc(Cl)c(Oc2cccc(N3CCNCC3)c2)s1]

or a pharmaceutically acceptable salt thereof.

3. The method according to claim 1, wherein the 3-($C_1$-$C_4$ alkyl)-benzyl is selected from 3-methylbenzyl, 3-ethylbenzyl, and 3-propylbenzyl.

4. The method according to claim 1, wherein the 3-($C_1$-$C_4$ alkyoxy) phenyl is selected from 3-methoxyphenyl, 3-ethoxyphenyl, and 3-propoxyphenyl.

5. The method according to claim 1, wherein the 4-($C_1$-$C_4$ alkyoxy)phenyl is selected from 4-methoxyphenyl, 4-ethoxyphenyl and 4-propoxyphenyl.

6. The method according to claim 1, wherein the 3-($C_1$-$C_4$ alkyoxy)benzyl is selected from 3-methoxybenzyl, 3-ethoxybenzyl, and 3-propoxybenzyl.

7. The method according to claim 1, wherein the 4-($C_1$-$C_4$ alkyoxy)benzyl is selected from 4-methoxybenzyl, 4-ethoxybenzyl, and 4-propoxybenzyl.

8. The method according to claim 1, wherein $R_5$ is selected from 4-methylpiperazin, 4-ethylpiperazin, and 4-propylpiperazin.

9. The method according to claim 1, wherein the naphthalene-($C_1$-$C_4$) alkyl is selected from naphthalene-1-yl-methyl, naphthalene-1-yl-ethyl, and naphthalene-1-yl-propyl.

* * * * *